United States Patent [19]

Nardella et al.

[11] Patent Number: 6,050,267
[45] Date of Patent: Apr. 18, 2000

[54] CATHETER POSITIONING SYSTEM

[75] Inventors: Paul C. Nardella, Wareham; Thomas A. Wrublewski, Sharon, both of Mass.

[73] Assignee: American Cardiac Ablation Co. Inc., Taunton, Mass.

[21] Appl. No.: 09/018,435

[22] Filed: Feb. 4, 1998

Related U.S. Application Data

[63] Continuation-in-part of application No. 08/847,684, Apr. 28, 1997.

[51] Int. Cl.[7] .................................................. A61B 19/00
[52] U.S. Cl. ............................................ 128/899; 600/547
[58] Field of Search ........................... 128/899; 600/547, 600/373, 382

[56] References Cited

U.S. PATENT DOCUMENTS

| | | | |
|---|---|---|---|
| 5,201,900 | 4/1993 | Nardella | 606/157 |
| 5,293,868 | 3/1994 | Nardella | 128/642 |
| 5,295,484 | 3/1994 | Marcus et al. | 128/660.03 |
| 5,341,807 | 8/1994 | Nardella | 128/642 |
| 5,357,956 | 10/1994 | Nardella | 128/642 |
| 5,364,392 | 11/1994 | Warner et al. | 606/34 |
| 5,383,917 | 1/1995 | Desai et al. | 607/702 |
| 5,409,000 | 4/1995 | Imran | 128/642 |
| 5,417,687 | 5/1995 | Nardella et al. | 606/32 |
| 5,443,489 | 8/1995 | Ben-Haim | 607/115 |
| 5,447,529 | 9/1995 | Marchlinski et al. | 607/99 |
| 5,514,130 | 5/1996 | Baker | 606/41 |
| 5,536,267 | 7/1996 | Edwards et al. | 606/41 |
| 5,540,655 | 7/1996 | Edwards et al. | 604/22 |
| 5,540,679 | 7/1996 | Fram et al. | 606/27 |
| 5,540,681 | 7/1996 | Strul et al. | 606/34 |
| 5,554,110 | 9/1996 | Edwards et al. | 604/22 |
| 5,573,533 | 11/1996 | Strul | 606/34 |
| 5,578,007 | 11/1996 | Imran | 604/95 |
| 5,697,377 | 12/1997 | Wittkampf | 128/696 |

OTHER PUBLICATIONS

*New Three Dimensional Localization Technique for Endocardial Electrodes*, American Heart Association, Abstracts from the 69th Scientific Sessions, New Orleans Convention Center, New Orleans, Louisiana, Nov. 10–13, 1996, Supplement to Circulation, vol. 94, No. 8, Oct. 15, 1996, three pages.

*Primary Examiner*—John P. Lacyk
*Attorney, Agent, or Firm*—Nutter, McClennen & Fish, LLP

[57] ABSTRACT

A system for detecting the position of a catheter in a patient includes three sets of excitation electrodes, with one set disposed in each of three intersecting axes. A signal processor measures a voltage indicative of impedance between a detection electrode disposed on the catheter and each of the three sets of excitation signals in order to determine the X coordinate, Y coordinate and Z coordinate of the catheter. The detected position of the catheter is recorded and the detection of subsequent catheter positions is performed relative to the recorded catheter position. The difference between subsequent catheter positions and the recorded position relative to the X, Y and Z axes is displayed in order to facilitate repositioning of the catheter at the recorded position. Excitation electrode embodiments utilizing as few as four excitation electrodes are disclosed. The excitation electrodes may be surface, subcutaneous or intracardiac electrodes.

21 Claims, 16 Drawing Sheets

CATHETER POSITIONING SYSTEM

CROSS REFERENCE TO RELATED APPLICATIONS

This application is a continuation-in-part application of U.S. patent application Ser. No. 08/847,684, filed Apr. 28, 1997, entitled Catheter Positioning System.

STATEMENTS REGARDING FEDERALLY SPONSORED RESEARCH

Not Applicable.

BACKGROUND OF THE INVENTION

Catheters of the type which are inserted into a vessel of a patient for carrying electrical signals to and from the patient are used in various applications. For example, cardiac catheters are inserted within a blood vessel into a patient's heart to detect cardiac electrical signals, to apply electrical stimulation for diagnostic testing and to apply treatment signals, such as tissue ablation signals which are used to eliminate the source of an arrhythmia. Other applications for ablation catheters include the treatment of tumors, such as breast or liver tumors, and the identification of tumor biopsy sampling sites. In addition to one or more electrodes, the catheter may include other structures, such as a lumen through which light, thermal energy or chemical agents are delivered and/or a sampling system for sampling a tissue or fluid specimen.

One multi-electrode catheter arrangement, described in U.S. Pat. No. 5,341,807 (Nardella), includes signal processing circuitry for detecting contact of the catheter with tissue, such as a vessel wall. The Nardella catheter includes a tip electrode and a plurality of ring electrodes spaced along the catheter. The differential voltage indicative of impedance between the electrodes is measured to provide an indication of the catheter electrodes being disposed in different mediums (for example, when one electrode is in blood and another is in contact with tissue). The resulting indication of catheter contact is useful in many applications. For example, in cardiac ablation, the catheter must be in contact with, or at least in close proximity to, the treatment site in order to ensure that an effective level of RF energy reaches the tissue.

It is generally necessary to utilize a visualization technique of some sort in order to guide the catheter to a desired site of diagnosis and/or treatment and to ensure that the catheter remains at the desired location. Additionally, it is often desirable or necessary to re-position the catheter at a particular location. For example, in applications in which a cardiac ablation catheter is used for diagnosis and subsequent treatment of an arrhythmia, the catheter is moved around the heart while cardiac electrical signals are monitored, following in which one or more sites identified as being the source of an arrhythmia are ablated. Thus, during such a procedure, it is necessary to determine the location of the catheter as the electrical signals are monitored in order to facilitate re-positioning the catheter at the site of an arrhythmia for ablation. Further, during any catheter procedure, the catheter may slip and require re-positioning in order to successfully complete the procedure.

Catheter positioning and re-positioning has conventionally been achieved with the use of fluoroscopic techniques. However, since fluoroscopy typically provides only two-dimensional information, its accuracy in catheter positioning is limited. Furthermore, due to the potential risks associated with exposure to electromagnetic radiation, it is advantageous to limit the use of fluoroscopy.

SUMMARY OF THE INVENTION

The invention relates to a catheter positioning system for detecting the position of a catheter relative to intersecting X, Y and Z axes and for permitting the catheter to be accurately re-positioned with an accuracy on the order of about one millimeter. Once the catheter is placed at a desired location, its position is recorded. Subsequent positions of the catheter are processed relative to the recorded position and are displayed. The catheter is re-positioned at the recorded position by moving the catheter until the displayed difference between the subsequent and recorded catheter positions decreases to zero. With this arrangement, once a desired location is detected and recorded, the fluoroscopic equipment can be turned off, thereby advantageously limiting the patient's exposure to potentially harmful radiation. Further, the accuracy with which the catheter is re-positioned is enhanced, as compared to the use of fluoroscopic techniques for this purpose.

The position detection system includes a first set of excitation, or reference electrodes disposed along the X axis, a second set of excitation electrodes disposed along the Y axis, and a third set of excitation electrodes disposed along the Z axis. A signal processor measures the differential voltage indicative of impedance between a detection electrode on the catheter and each electrode of the first, second and third sets of excitation electrodes to determine the X coordinate, Y coordinate and Z coordinate of the catheter position, respectively. To this end, a first current provided by an energy source flows between the first set of excitation electrodes, a second current flows between the second set of excitation electrodes and a third current flows between the third set of excitation electrodes.

Preferably, the first, second and third currents have different frequencies which minimize any cross-axis interference.

The signal processor includes an X axis processor unit coupled to the first set of excitation electrodes, a Y axis processor unit coupled to the second set of excitation electrodes and a Z axis processor unit coupled to the third set of excitation electrodes. Each of the processor units includes a demodulator coupled to the output of a differential amplifier for providing a DC signal proportional to the position of the catheter relative to the respective axis (i.e., the coordinate).

In one embodiment, the differential voltage indicative of impedance is measured by detecting the difference between the voltage at the detection electrode and a reference potential generated from each of the three sets of excitation electrodes. Specifically, an X axis reference node is provided by a resistor divider coupled between the X axis excitation electrodes and used to detect catheter position along the X axis by measuring the voltage between the detection electrode and the X axis reference potential. Similarly, a Y axis reference potential is provided by a resistor divider coupled between the Y axis excitation electrodes and used to detect catheter position along the Y axis by measuring the voltage between the detection electrode and the Y axis reference potential and a Z axis reference potential is provided by a resistor divider coupled between the Z axis excitation electrodes and used to detect catheter position along the Z axis by measuring the voltage between the detection electrode and the Z axis reference potential.

In another embodiment, catheter position detection measurements along each of the three axes are strict differential measurements made without the use of a reference potential or a separate reference electrode. For each of the three axes, a first amplifier measures the voltage between the detection electrode and one electrode of a excitation electrode pair for the given axis and a second amplifier measures the voltage between the detection electrode and the other one of the pair of excitation electrodes. A differential amplifier coupled to the outputs of the first and second amplifiers provides an output signal indicative of the position of the detection electrode relative to the excitation electrodes.

An optional EKG sensor detects an EKG signal of the patient for use in synchronizing detection of the catheter position. Further, an optional respiratory sensor detects a respiratory signal of the patient for use in synchronizing detection of the catheter position. In this way, artifacts due to cardiac motion and/or respiratory motion of the patient are reduced, thereby enhancing the accuracy of the catheter position detection.

The excitation, or reference electrodes may be subcutaneous electrodes, such as needle electrodes inserted into the patient's body in the region of catheter treatment or, alternatively, may be pad electrodes attached externally to the patient's body. In the later case, an additional set of electrodes, referred to as compensation electrodes, may be positioned along each of the X, Y and Z axes in order to compensate for any impedance effects due to external attachment of the pad electrodes.

As a further alternative, the excitation electrodes may be intracardiac electrodes. One suitable type of intracardiac electrode has a plurality of electrode supporting members at a distal end which, in use, are bowed outward to form a basket structure. The intracardiac electrode may support various numbers of excitation electrodes for applying three excitation signals along three intersecting axes.

In one embodiment, an intracardiac catheter supports eight or more electrodes which are grouped to define at least two X, Y, Z coordinate systems. This arrangement permits the signal processor to switch between excitation coordinate systems as the detection electrode approaches a region of large electric field non-linearity near one of the active excitation electrodes.

Also described is a catheter positioning system utilizing as few as four electrodes, either of the surface, subcutaneous, or intracardiac type or some combination thereof, for applying three excitation signals along three intersecting axes. One of the excitation electrodes provides an X axis electrode, one of the excitation electrodes provides a Y axis electrode and one of the electrodes provides a Z axis electrode. The fourth electrode is a "common" electrode shared by each of the three axis electrodes.

In one embodiment, the detection electrode is positioned at the tip of the catheter and the catheter further includes a proximal electrode and a reference electrode positioned between the tip and the proximal electrode. Contact of the catheter with tissue, such as a vessel wall, is detected by measuring the differential voltage indicative of impedance between the tip electrode and the proximal electrode relative to the reference electrode.

DETAILED DESCRIPTION OF THE INVENTION

Figure 1:
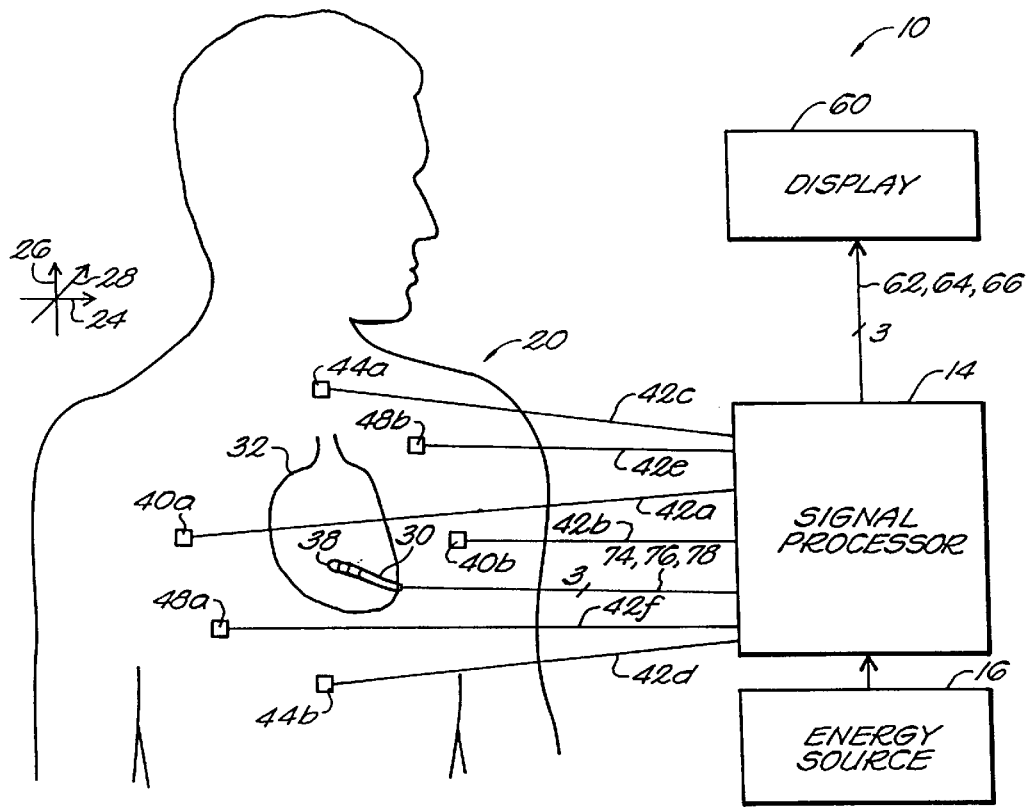
FIG. 1 illustrates a catheter positioning system in accordance with the invention.

Referring to FIG. 1, a catheter positioning system 10 for detecting the position of a catheter 30 having a detection electrode 38 is shown. The system 10 includes a signal processor 14 and three pairs of excitation, or reference electrodes 20, with one pair positioned along each of three intersecting axes, including the X axis 24, the Y axis 26 and the Z axis 28. Preferably, the three intersecting axes are mutually orthogonal, although they need not be, as discussed below. More particularly, a first set of excitation electrodes 40a, 40b is positioned along the X axis 24, a second set of excitation electrodes 44a, 44b is positioned along the Y axis 26, and a third set of excitation electrodes 48a, 48b is positioned along the Z axis 28. An energy source 16 supplies electrical energy to the excitation electrodes 20. A display 60, coupled to the signal processor 14, displays the detected catheter position in a manner that facilitates catheter re-positioning, as will be described. In applications in which the detection electrode 38 delivers ablation energy, the electrode may be referred to as an active electrode.

The illustrated catheter 30 is a cardiac ablation catheter adapted for insertion through a vessel into a patient's heart 32 for arrhythmia diagnosis and ablation. It will be appreciated by those of ordinary skill in the art, however, that the catheter positioning system 10 and related techniques described herein are suitable for use with any catheter application in which it is advantageous to re-position the catheter at a particular location.

The reference electrodes 20 may be subcutaneous electrodes, such as needle electrodes adapted for insertion into the patient's body. Alternatively, the reference electrodes 20 may be electrode pads, or patches adapted for external attachment to the patient's skin. Where the electrodes are externally attached, three additional sets of electrodes, referred to as compensation electrodes, may be provided to compensate for any impedance effects associated with attachment of the pads to the patient's skin, as will be described further in conjunction with FIG. 9. As a further alternative, the reference electrodes 20 may be intracardiac electrodes, as described in conjunction with FIGS. 11–14.

Each of the excitation electrodes 20 is electrically coupled to the signal processor 14 via a respective signal line 42a–42f, as shown. In the illustrative embodiment, the catheter 30 is coupled to the signal processor 14 via three signal lines 74, 76 and 78, with one signal line coupled to each electrode on the catheter, as described below in conjunction with FIG. 1A.

The energy source 16 delivers AC energy, referred to herein as an excitation signal, in the form of voltage or current to the electrodes via the signal processor 14 in order to permit voltage measurements to be made by the signal processor. The measured voltage is indicative of impedance since voltage is proportional to impedance. In the illustrative embodiment, the energy source 16 provides a first excitation current to the first set of excitation electrodes 40a, 40b, a second excitation current to the second set of excitation electrodes 44a, 44b and a third excitation current to the third set of excitation electrodes 48a, 48b.

Preferably, each of these currents has a different frequency chosen to minimize any cross-axis interference. In one example, the first current is a 48 KHz AC current, the second current is a 50 KHz AC current and the third current is a 54 KHz AC current. In alternative embodiments, other distinguishing characteristics of the currents may be varied among the three axes to sense and differentiate the respective current signals. Distinguishing characteristics may include, for example, phase or timing variations between the current signals for each axis.

Signal processor 14 measures the differential voltage indicative of impedance between the detection electrode 38 of the catheter 30 and each of the six excitation electrodes 20 in order to determine the three-dimensional position of the catheter 30 and, specifically, to determine the X coordinate, Y coordinate and Z coordinate of the catheter 30. To this end, the signal processor 14 includes an X axis processor unit 50, a Y axis processor unit 52 and a Z axis processor unit 54 (FIG. 2), with each processor unit measuring the differential voltage indicative of impedance between the detection electrode 38 and each one of the electrodes of the respective set of electrodes. For example, the X axis processor unit 50 measures the voltage indicative of impedance between the detection electrode 38 and excitation electrode 40a and also between detection electrode 38 and excitation electrode 40b in order to determine the X coordinate of the catheter 30 (i.e., the position of the catheter relative to the X axis).

The signal processor 14 provides an X axis output signal 62, a Y axis output signal 64 and a Z output axis signal 66 coupled to the display 60, which may be referred to alternatively as the catheter location map. The display 60 provides an indication of the position of the catheter relative to the X, Y and Z axes and/or relative to a previously recorded position. More particularly, the catheter positioning system 10 is capable of operating in a "direct" mode of operation, during which the catheter position is continuously tracked and an indication thereof is displayed, or in a "relative" mode of operation, in which a position of the catheter is recorded, subsequent position measurements are made relative to the recorded position and the difference between the recorded and subsequent positions is displayed, as will be described further below.

The display 60 may take various forms, including analog or digital. In one embodiment, two axes are displayed on one graph and the third axis is displayed on a separate device, such as a digital meter. Alternatively, a three axis graphical representation, a wire frame representation, or a surface rendering technique, all of which are conventional Computer-Aided Design (CAD) system presentations, may be used to provide the display 60.

Figure 1A:
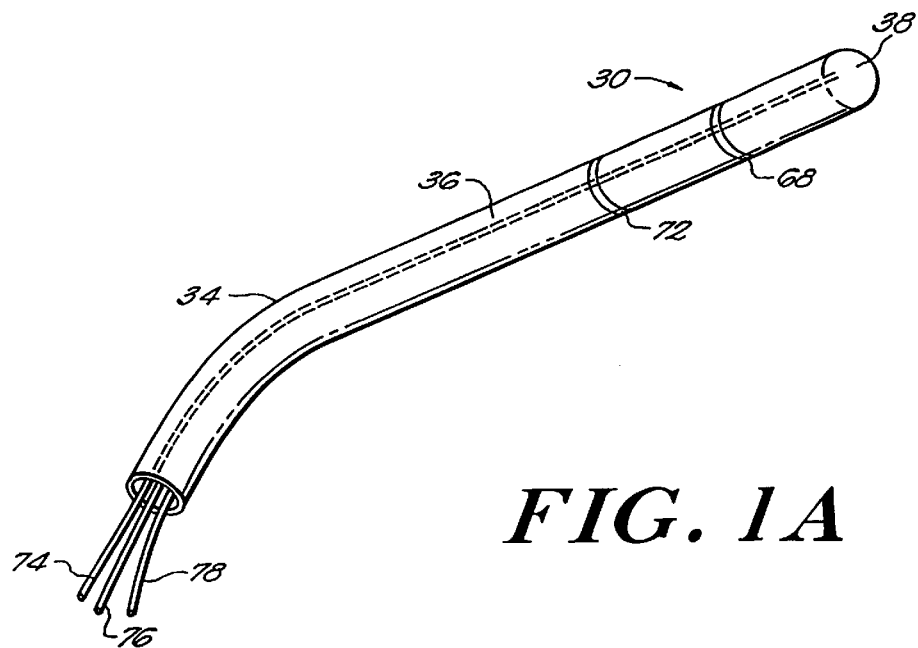
FIG. 1A is a perspective view of a multi-electrode catheter for use with the catheter positioning system of FIG. 1.

Referring also to FIG. 1A, an enlarged view of the illustrative cardiac ablation catheter 30 is shown. The detection electrode 38 which may deliver ablation energy is positioned at the distal tip of the catheter and thus, may be referred to as the tip electrode 38. The catheter 30 further includes a proximal electrode 72 and a reference electrode 68 disposed between the proximal electrode and the tip electrode, with the proximal and reference electrodes being in the form of ring electrodes, as shown. The catheter 30 has an elongated insulating body 36 mounted at the end of a flexible tube 34 which is used for inserting and manipulating the catheter along a vessel. Signal lines 74, 76, and 78 extend from the tube 34 to electrically connect catheter electrodes 38, 68 and 72 to the signal processor 14, respectively. In accordance with a feature of the invention, a fourth current provided by the energy source 16 flows between the tip electrode 38 and proximal electrode in order to facilitate measurements used to determine catheter contact, as described below in conjunction with FIG. 8.

Figure 2:
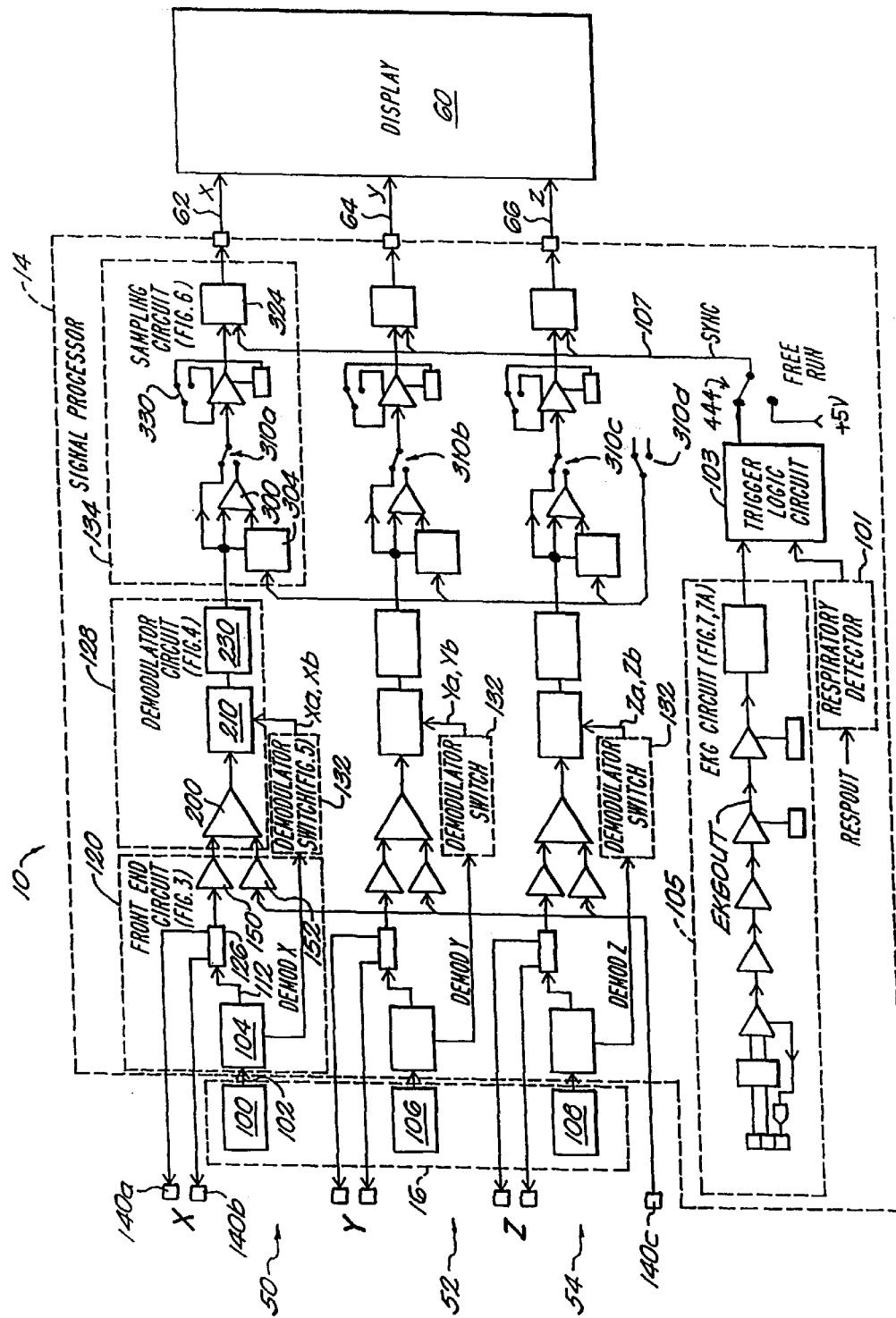
FIG. 2 is block diagram of the catheter positioning system of FIG. 1.

Referring also to FIG. 2, a block diagram of the catheter positioning system 10 is shown to include the signal processor 14, energy source 16 and display 60. The energy source 16 includes three oscillators 100, 106 and 108 for providing the first current to the X axis excitation electrodes 40a, 40b, the second current to the Y axis excitation electrodes 44a, 44b and the third current to the Z axis excitation electrodes 48a, 48b, respectively.

The signal processor 14 includes the X axis processor unit 50 which is coupled to the X axis excitation electrodes 40a, 40b, the Y axis processor unit 52 which is coupled to the Y axis excitation electrodes 44a, 44b, and the Z axis processor unit 54 which is coupled to the Z axis excitation electrodes 48a, 48b, all of which are substantially identical in construction. The processor units will be described with reference to exemplary X axis processor unit 50 for simplicity of discussion. Also provided in the signal processor 14 is an optional EKG circuit 105 (FIGS. 7 and 7A) which monitors the EKG signal of the patient and an optional respiratory detector 101 which monitors the respiratory signal of the patient. The output signals from the EKG circuit 105 and the respiratory detector 101 are processed by a trigger logic circuit 103 to provide a SYNC signal 107 which is used to synchronize catheter position detection, as will be described.

Figure 5:
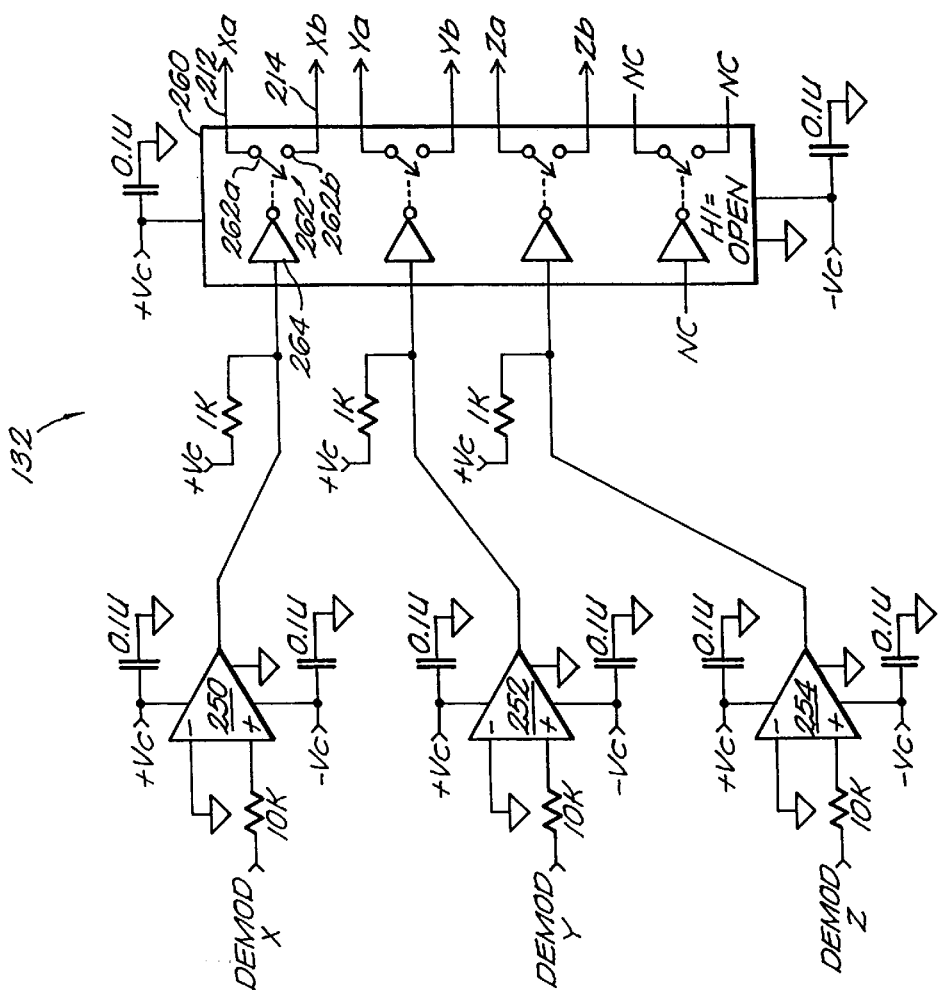
FIG. 5 is a schematic of the demodulator switch of the catheter positioning system of FIG. 2.
Figure 6:
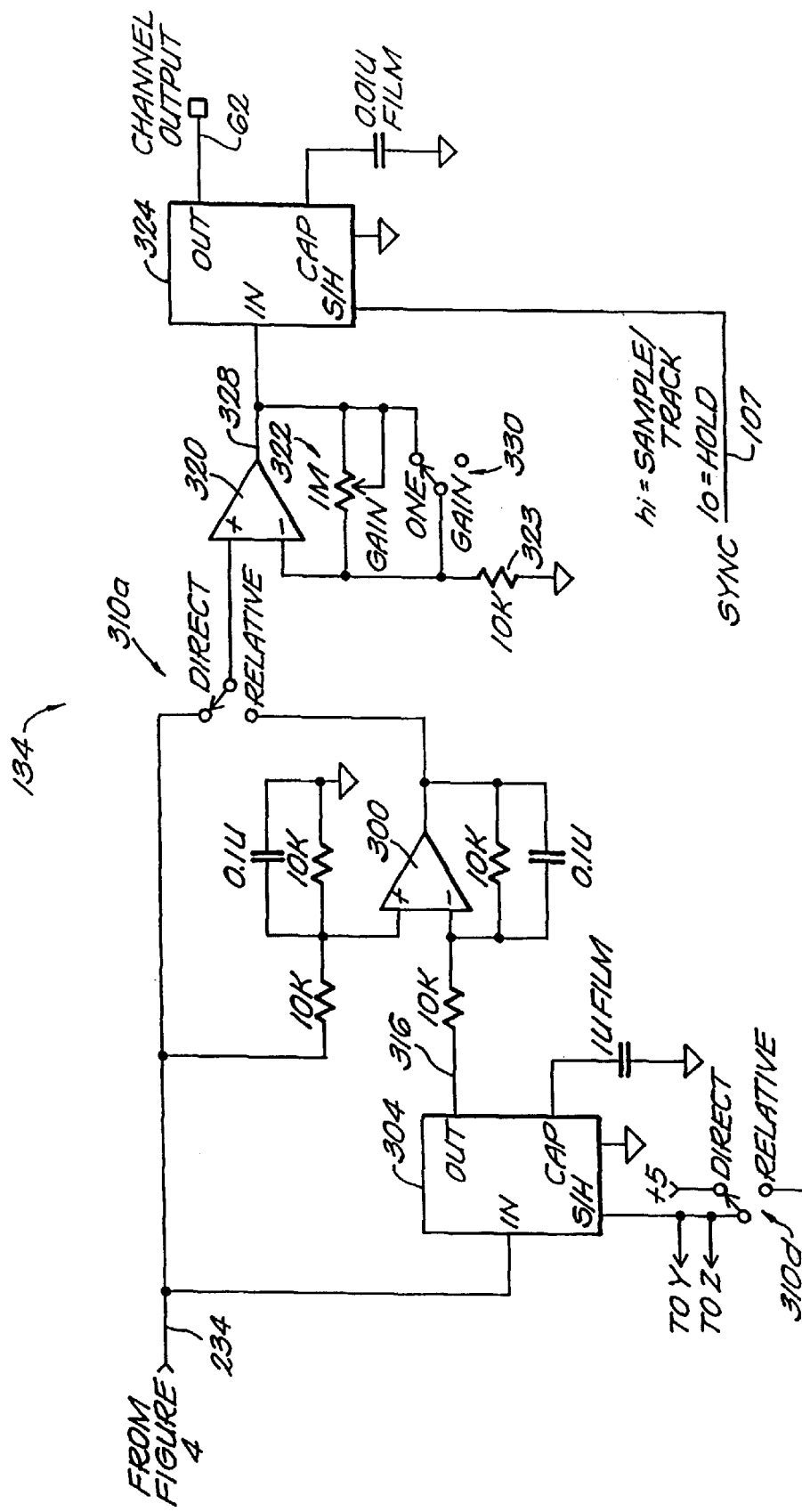
FIG. 6 is a schematic of the sampling circuit of the catheter positioning system FIG. 2.

The processor unit 50 includes a front end circuit 120 (FIG. 3) coupled to the excitation electrodes 40a, 40b via respective terminals 140a, 140b of a connector 140, a demodulator circuit 128 (FIG. 4) coupled to the outputs of the front end circuit 120 and a sampling circuit 134 (FIG. 6). The demodulator circuit 128 is responsive to a demodulator switch 132 (FIG. 5). The sampling circuit 134 provides the X axis output signal 62 to the display 60, as shown. It will be appreciated by those of ordinary skill in the art that the particular circuitry arrangement and component values described herein are illustrative only and may be varied without departing from the spirit from the invention.

Figure 3:
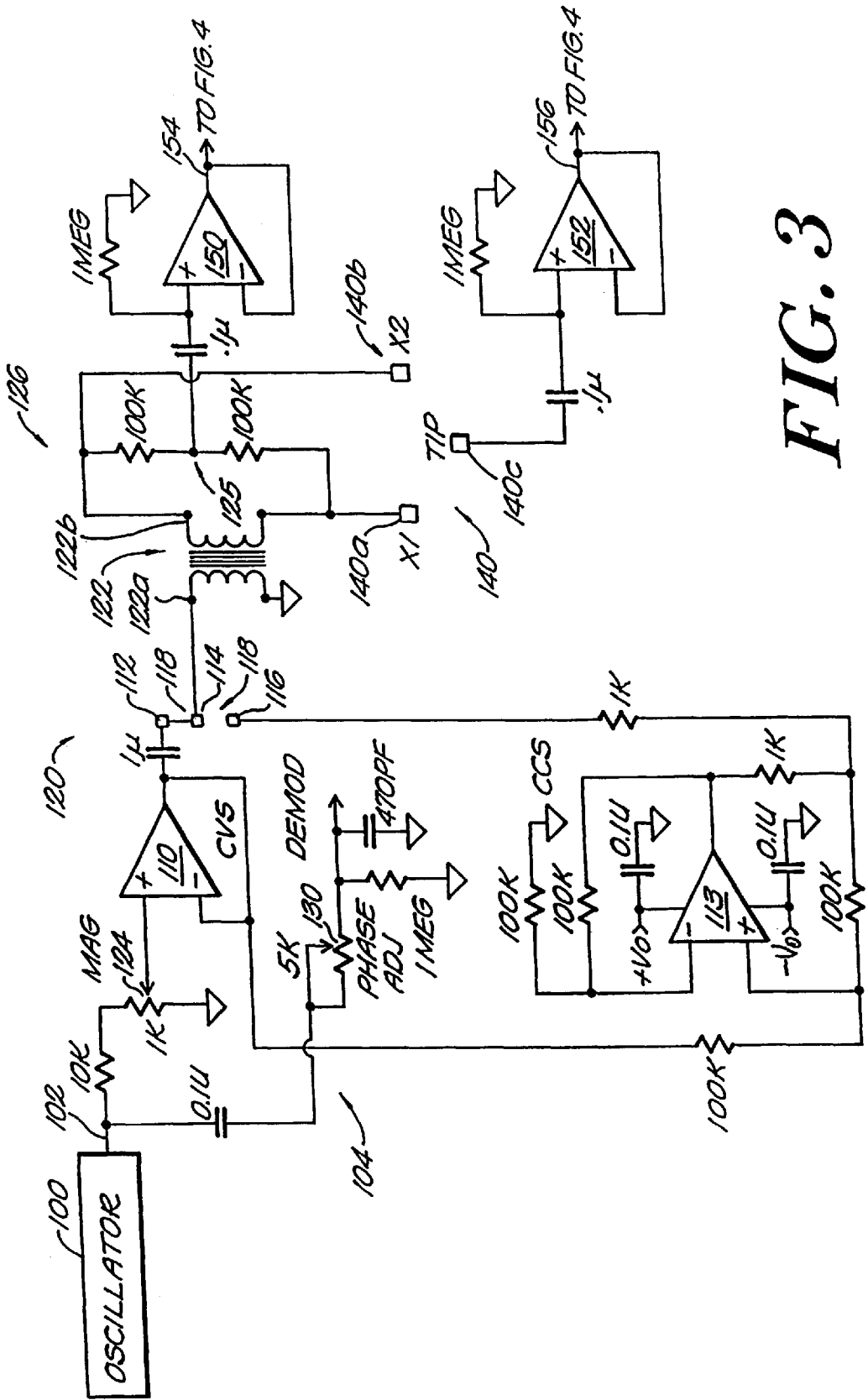
FIG. 3 is a schematic of the front end circuit of the catheter positioning system of FIG. 2.

Referring also to FIG. 3, the front end circuit 120 includes a gain and/or phase stage 104, an electrode interface 126 and buffers 150, 152. The output signal 102 from the axis oscillator 100 is coupled to the gain and/or phase stage 104 which permits the magnitude of the AC energy signal 102 and/or the phase of demodulation of the signal from the X axis excitation electrodes 40a, 40b to be adjusted. More particularly, the oscillator output signal 102 is coupled to a first potentiometer 124 which can be adjusted to vary the magnitude of the oscillator output signal 102. The oscillator output signal 102 is further coupled to a second potentiometer 130 which is adjustable to vary the phase of demodulation of the signal from the excitation electrodes 40a, 40b. More particularly, the output of the potentiometer 130 provides a phase signal (DEMODX) which is coupled to the demodulator switch 132 (FIG. 5). The phase signal is used to vary the demodulation phase in order to compensate for phase shifts resulting from signal processing.

The magnitude setting potentiometer 124 is coupled to an operational amplifier 110 which provides a voltage output signal at a circuit node 112. The output of voltage amplifier 110 is further coupled to an operational amplifier 113 which provides a current output signal at a circuit node 116. A jumper 118 is provided for selectively connecting either the voltage output of amplifier 110 or the current output of amplifier 113 to a circuit node 114. With this arrangement, the jumper 118 can be positioned in order to provide an AC current or an AC voltage to the excitation electrodes 40a, 40b. In the preferred embodiment, an AC current is supplied to the excitation electrodes 40a, 40b, since this stimulus type provides a larger signal-to-noise ratio.

A transformer 122 coupled to the circuit node 114 isolates the oscillator 100 on the primary side 122a of the transformer from the reference electrodes 40a, 40b coupled to the secondary side 122b of the transformer. The X axis reference electrodes 40a, 40b are coupled to the signal processor 14 via respective terminals 140a, 140b of connector 140, as shown. More particularly, the terminals 140a, 140b are coupled to a buffer 150 via a resistor divider 125. The detection electrode 38 of the catheter 30 is coupled to the signal processor 14 via terminal 140c of connector 140. A buffer 152 buffers the electrical signal from the detection electrode 38.

The front end circuit 120 also includes a differential amplifier 200 having a first input coupled to output 154 of buffer 150 and a second input coupled to the output 156 of buffer 152. The output signal 158 of the differential amplifier 200 is coupled to demodulator circuit 128 (FIG. 4).

Figure 4:
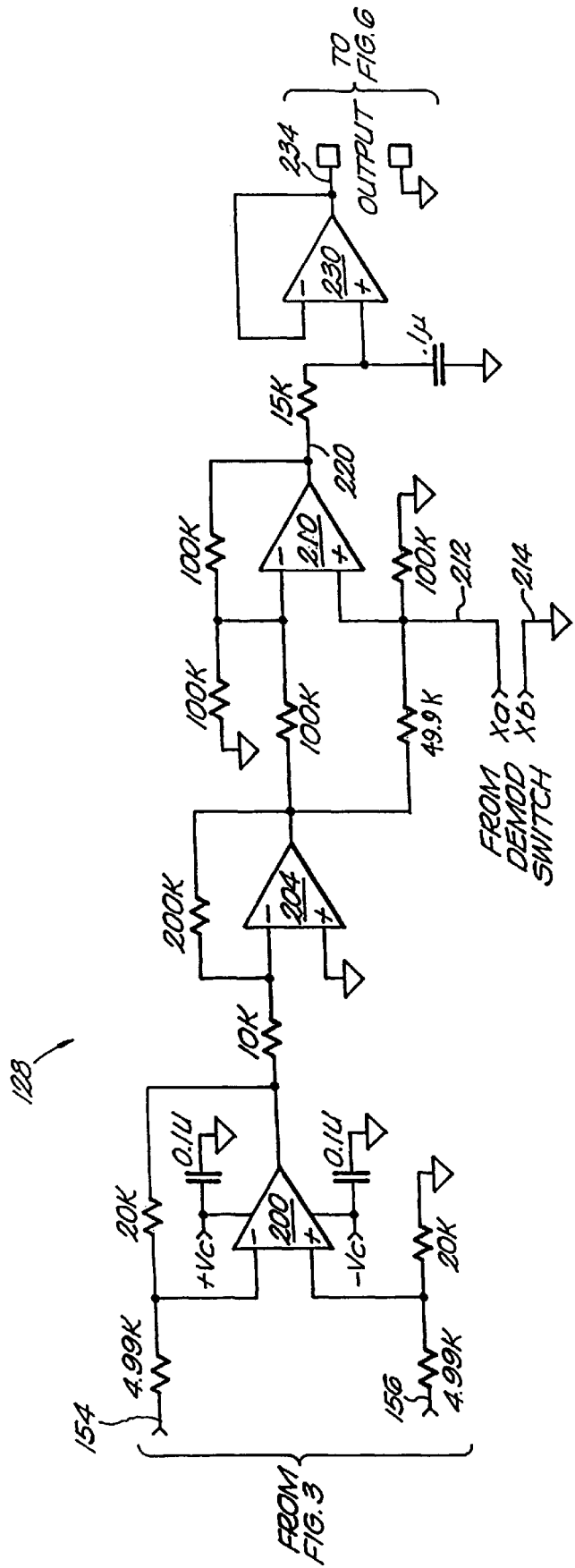
FIG. 4 is a schematic of the demodulator circuit of the catheter positioning system of FIG. 2.

Referring to FIG. 4, the demodulator circuit 128 includes a gain stage 204 having an input coupled to output 158 of differential amplifier 200, as shown. Demodulation is provided by an amplifier 210 having an inverting input coupled to the output of the gain stage 204 and a non-inverting input coupled to the output of the gain stage 204 and further to a signal line 212 from the demodulator switch 132, as will be described below in conjunction with FIG. 5.

In operation, the differential voltage indicative of impedance between the excitation electrodes 40a, 40b and the detection electrode 38 is measured by differential amplifier 200 such that the output of amplifier 200 is an AC signal having a phase and magnitude indicative of the position of the detection electrode 38 relative to the excitation electrodes 40a, 40b. That is, an output signal in phase with the excitation stimulus indicates that the detection electrode 38 is closer to one of the electrodes 40a, 40b and an output signal out of phase with the excitation stimulus indicates that the detection electrode 38 is closer to the other one of the electrodes 40a, 40b. Thus, when the output signal of the amplifier 200 is null, the detection electrode 38 is equidistantly positioned between the X axis excitation electrodes 40a, 40b. The magnitude of the output signal of the amplifier 200 indicates the relative proximity of the detection electrode 38 to each of the excitation electrodes 40a, 40b.

The gain of the output signal of amplifier 200 is boosted by the gain stage 204 in order to enhance the detection sensitivity. For example, in the illustrative embodiment, the gain is boosted by a factor of twenty. The output of the gain stage 204 is demodulated by demodulator 210 in accordance with signals Xa and Xb provided by the demodulator switch 132 (FIG. 5) in response to the respective phase signal DEMODX, as will be described.

Consideration of FIGS. 3 and 4 reveals that catheter position detection along the X axis (i.e., the measurement of the differential voltage indicative of impedance between the detection electrode and each of the X axis excitation electrodes 40a, 40b) is achieved by measuring the voltage between the detection electrode 38 and an electronically generated reference potential at the center of the resistor divider 125. That is, the voltage at the center of the resistor divider 125 is equal to one-half of the voltage between the X axis excitation electrodes 40a and 40b. The same signal measurement technique is used to detect catheter position relative to the Y and Z axes. Thus, for each of the three axes, a "virtual" or electronic reference potential is generated for measuring the signal at the detection electrode.

The voltage at the center of resistor divider 125 need not be equal to one half of the voltage between the X axis excitation electrodes 40a and 40b. While the one half value may be preferred for certain electrode configurations, this voltage may be varied to any level between the X axis excitation electrodes 40a and 40b. In fact, measurement of the differential voltage indicative of impedance between the detection electrode and the X axis may be achieved by measuring the voltage between the detection electrode and either of the X axis excitation electrodes 40a or 40b directly without the use of resistor divider 125. Accordingly, the reference potential may be varied in any amount from the voltage of one axis excitation electrode to the voltage of the other excitation electrode for that axis.

This technique advantageously permits elimination of a separate additional reference electrode to be placed on the surface of the patient which could move and render the catheter position detection inaccurate. Further, such an additional reference electrode has noise associated with its use.

This arrangement is also advantageous as compared to the use of a separate reference electrode provided in the form of an intracardiac electrode since such an intracardiac electrode is susceptible to movement within the body due to the forces applied to the electrode by a beating heart. In addition, an intracardiac reference electrode is a low impedance electrode that will create an equipotential field based upon its size, shape and location within the heart. As a result, position detection of the detection electrode suffers from reduced sensitivity when the detection electrode nears the equipotential field. This reduced sensitivity is most significant when the intracardiac reference electrode and the detection electrode are located within the same chamber of a heart.

Figure 4A:
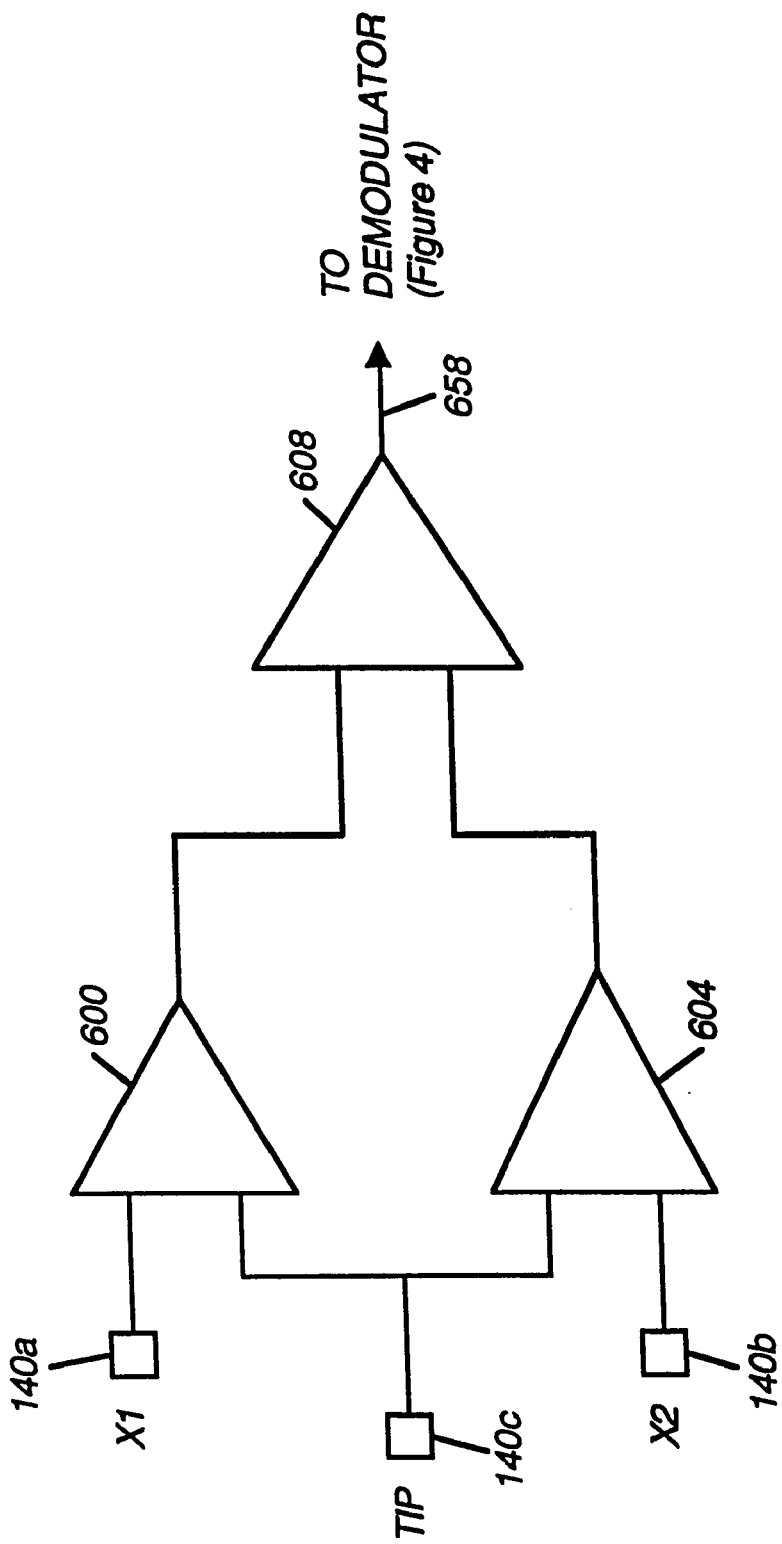
FIG. 4A is an alternative differential voltage circuit for the front end circuit for the catheter positioning system of FIG. 2.

Referring to FIG. 4A, an alternative technique for measuring the differential voltage indicative of impedance between the detection electrode 38 and each of the X axis excitation electrodes 40a, 40b is shown. This technique does not require the use of a separate reference electrode for attachment to, or insertion into the patient or "virtual" reference nodes as described above. The voltage difference between the detection electrode 38 and a first one of the X axis excitation electrodes 40a is measured with an amplifier 600 and the voltage difference between the detection electrode 38 and the other X axis excitation electrode 40b is measured with an amplifier 604. The outputs of amplifiers 600 and 604 are coupled to inputs of a differential amplifier 608 which detects the differential voltage between the detection electrode and the X axis electrodes, thereby indicating the location of the detection electrode relative to such excitation electrodes 40a, 40b. Thus, the output 658 of amplifier 608 is null when the detection electrode is located equidistantly between the X axis, excitation electrodes. The output 658 of amplifier 608 may then be coupled to demodulation circuit 128 in place of signal 158 (FIG. 4).

Referring also to FIG. 5, the demodulator switch 132 provides demodulation input signals Xa/Xb, Ya/Yb and Za/Zb to the processor units 50, 52, and 54, respectively, as shown in FIG. 2. The demodulator switch 132 is responsive to phase signals DEMODX, DEMODY and DEMODZ (FIG. 2) from the phase portion of circuitry 104 of the front-end circuit 120 of each the X, Y and Z processor units 50, 52 and 54. More particularly, each of the DEMOD signals is coupled to a respective comparator 250, 252 and 254, as shown and the output of each of the comparators 250, 252, and 254 is coupled to an analog switch 260.

Switch 260 includes three inverters, each having an input coupled to an output of a respective one of the comparators 250, 252, 254. For example, the output of the X axis comparator 250 is coupled to the input of inverter 264. Each inverter has a switch associated therewith that is adapted for being in a first, open position when the inverter output signal is in one logic state and in a second, closed position when the inverter output signal is in the second logic state. In the illustrative example, when the output signal of the inverter 264 is at a logic low level, the switch 262 is open, so that terminals 262a and 262b are disconnected, as shown. When the inverter output signal is at a logic high level, the corresponding switch 262 is closed, with terminals 262a and 262b electrically connected.

Referring again to FIG. 4, switch 262 is coupled between signal lines 212 and 214 such that, when the switch 262 is closed, signal line 212 is connected to ground via signal line 214. Whereas, when the switch 262 is open, signal line 212 is floating. With this arrangement, the signal provided at the output of amplifier 204 is demodulated with respect to the phase signal (DEMODX). The output signal 220 of the demodulator 210 is thus a DC signal with varying amplitude having a mean value proportional to the position of the catheter 30 relative to the X axis (i.e., proportional to the X coordinate). An amplifier 230 forms a low-pass filter for establishing the mean value, in order to enhance the detection accuracy of the system. The filter output signal 234, referred to alternatively as the demodulated catheter position signal 234, is coupled to the sampling circuit 134 (FIG. 6). The information from channels Y 52 and Z 54 present on channel X are also demodulated. However, since they are not synchronous with the demodulation signal, an AC signal is generated and this information is averaged to zero by the filter.

Referring to FIG. 6, the sampling circuit 134 controls the sampling of the demodulated catheter position signal 234 (FIG. 4) in order to generate the X axis output signal 62. More particularly, as noted above, the catheter positioning system 10 is adapted for operating in a "direct" mode of operation, during which the catheter position is continuously tracked, or in a "relative" mode of operation, in which the catheter position is recorded and subsequent catheter positions are detected relative to the recorded position.

To this end, a four-pole, double throw direct/relative switch 310 is provided for user control in order to select between the direct and relative modes of operation. Switch pole 310a is associated with the X axis processor unit 50 (FIG. 6), pole 310b is associated with the Y axis processor unit 52 (FIG. 2) and pole 310c is associated with the Z axis processor unit 54 (FIG. 2). The fourth pole 310d of the switch 310 is common to all three of the processor units and is provided for controlling the sample and hold circuit 304, as will be described.

The demodulated catheter position signal 234 is coupled to a differential amplifier 300, the input of sample and hold circuit 304 and switch 310a, as shown. The output of the sample and hold circuit 304 is coupled to an input of the differential amplifier 300, the output of which is coupled to the switch 310a. Switch 310a selectively couples the non-inverting input of a gain stage 320 either to the catheter position signal 234 or to the output of operational amplifier 300. When the switch 310 is in the direct position, as shown, the non-inverting input of the gain stage 320 is coupled to the demodulated catheter position signal 234. Alternatively, when the switch 310 is in the relative position, the non-inverting input of gain stage 320 is coupled to the output of the amplifier 300. The output signal of amplifier 300 represents the catheter's position relative to the catheter's position when the switch 310 was in the direct position.

Switch 310d causes the S/H input of the sample and hold circuit 304 to be selectively coupled to +5V or to ground, as shown. When the switch 310 is in the direct position and the S/H input to the sample and hold circuit 304 is at +5V, the sample and hold circuit 304 tracks the signal 234 to provide output signal 316. When the switch 310 is in the relative position and the S/H input to the sample and hold circuit 304 is at ground, the output signal 316 of the sample and hold circuit 304 is held constant.

The gain of the operational amplifier 320 is adjustable in order to adjust the position detection sensitivity. To this end, a switch 330 is provided in feedback relationship with the gain stage 320 to selectively connect or disconnect the output of gain stage 320 to its inverting input. In this way, the gain of amplifier 320 can be set to one or to a gain set by resistors 322 and 323.

The output signal 328 of the gain stage 320 is coupled to the input of a sample and hold circuit 324 which is operative to track and sample the signal 328 in accordance with the SYNC signal 107. This sampling stage serves to reduce artifacts associated with the patient's EKG and/or respiratory signals, as will be described. The output of the sample and hold circuit 324 is a DC signal 62 (FIG. 2) indicative of the X coordinate of the catheter position during the direct mode of operation or indicative of the difference between the X coordinate of the catheter position and a recorded catheter position during the relative mode of operation. Thus, the display 60 can display the catheter position relative to a previous position or the direct catheter position measurements relative to an arbitrary origin. For example, multiple catheter positions relative to the X, Y and Z axes may be captured and displayed.

In operation, when the switch 310 is in the direct position, the demodulated catheter position signal 234 is tracked by the sample and hold circuit 304 and is coupled to the gain stage 320 for processing and coupling to the input of the sample and hold circuit 324. The signal 328 is thus indicative of the present X coordinate of the catheter and is sampled by the circuit 324 every time the SYNC signal 107 transitions to a logic high level.

When the switch 310 is toggled to the relative position, the sample and hold circuit 304 causes the previously tracked catheter position signal 234 to be held to provide the output signal 316. Further, the output of the differential amplifier 300 is coupled to the gain stage 320 for processing and coupling to the sample and hold circuit 324. In this mode of operation, the signal 328 is indicative of the difference between the present X coordinate of the catheter (i.e., as represented by the catheter position signal 234) and its position at the time that the switch 310 was toggled (i.e., as represented by the value held at the output 316 of the sample and hold circuit 304). Stated differently, the differential amplifier 300 detects the difference between the signal 316 which is indicative of the catheter X coordinate when the switch 310 was toggled (i.e., the recorded position) and the X coordinate of the present catheter position (i.e., the subsequent position) and it is this difference signal that is coupled to the gain stage 320 and to the sample and hold circuit 324 to provide the X axis output signal 62 to the display 60.

Figure 7:
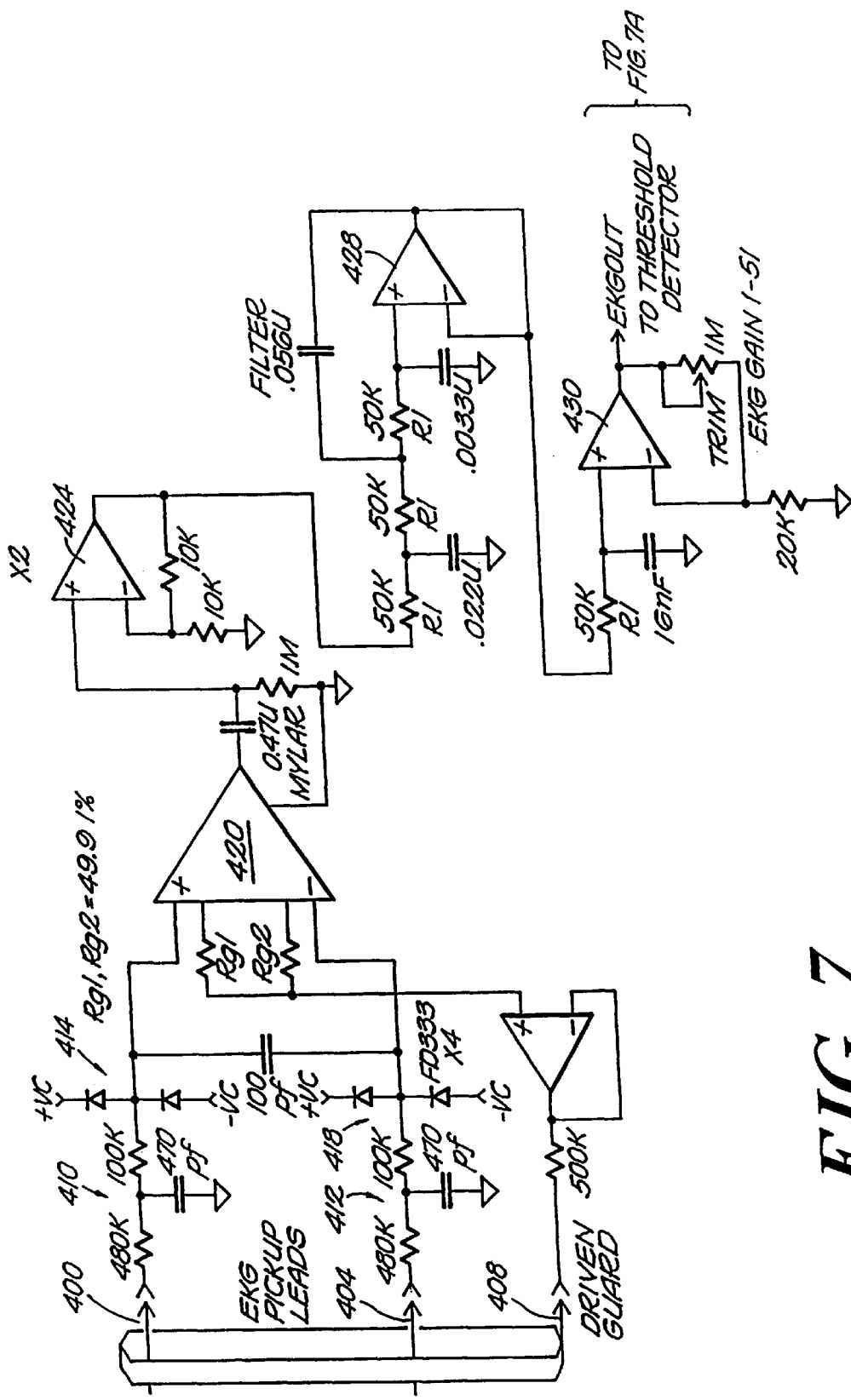
FIG. 7 is a schematic of a first portion of the EKG circuit of the catheter positioning system of FIG. 2.
Figure 7A:
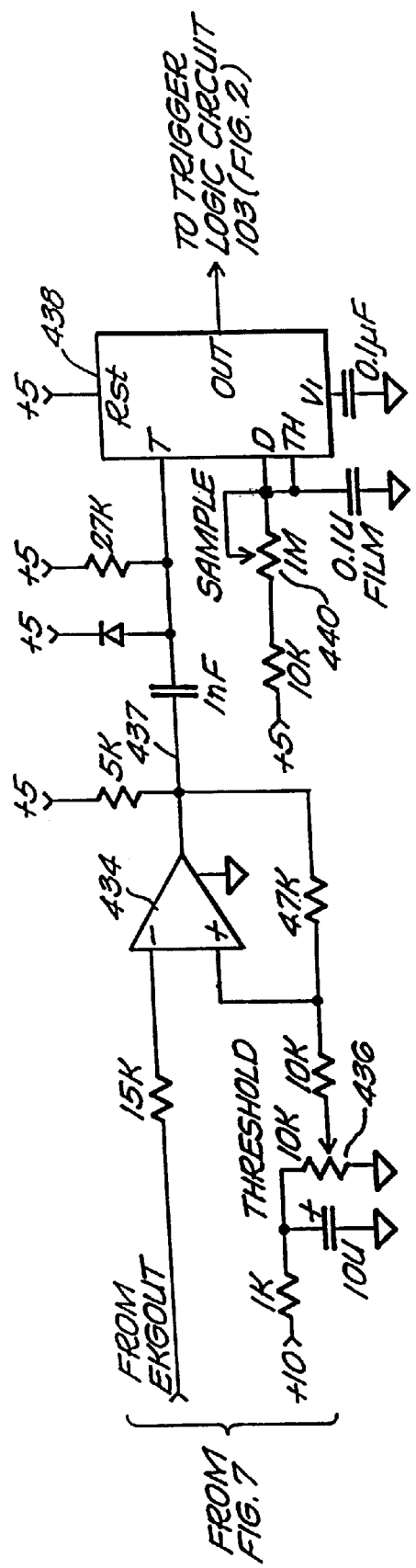
FIG. 7A is a schematic of a second portion of the EKG circuit of the catheter positioning system of FIG. 2.

Referring to FIGS. 7 and 7A, the EKG circuit 105 (FIG. 2) is shown to include three leads 400, 404 and 408 adapted for attachment to the patient. Two of the leads 400 and 404 are pickup leads and the third lead 408 is a guard, or reference lead. The leads 400 and 404 are coupled to respective filter circuits 410 and 412 and to optional protection devices 414 and 418, as shown. The filtered signals are further coupled to a differential amplifier 420.

The output of the differential amplifier 420 is coupled to an amplifier 424 for signal amplification and further to a low-pass filter 428. The output of filter 428 is coupled to an adjustable gain stage 430 to provide an output signal EKGOUT, as shown. In the illustrative embodiment, the gain can be adjusted from between one and fifty-one.

The EKGOUT signal is coupled to a first input of a threshold detection comparator 434 (FIG. 7A), the second input to which receives an adjustable threshold voltage. More particularly, the threshold voltage is adjustable with a potentiometer 436. The output signal 437 of the comparator 434 is a logic signal for triggering a one shot 438. Preferably, the threshold level coincides with the r-wave of the detected EKG signal. It will be appreciated by those of ordinary skill in the art that the EKG detection circuitry shown and described herein is illustrative only and that other conventional EKG triggering circuitry and techniques could alternatively be used.

The one-shot circuit 438 generates a sampling pulse at a duration set by an adjustable resistor 440. The output of the one-shot 438 provides an EKG trigger signal which transitions to a logic high level when the detected EKG signal exceeds the predetermined threshold level (i.e., when an r-wave is detected). The EKG trigger signal is coupled to a trigger logic circuit 103 (FIG. 2) or, in applications in which the SYNC signal 107 is based only on the EKG signal, the output of the EKG trigger signal is coupled directly to a switch 444 (FIG. 2).

The optional respiratory detector 101 (FIG. 2) includes similar circuitry and uses similar techniques to those described above in conjunction with EKG signal detection in order to detect the patient's respiratory signal. The output signal from the respiratory detector 101 is coupled to the trigger logic circuit 103 which combines the EKG trigger signal and the respiratory trigger signal to provide the SYNC signal 107 which indicates a predetermined point in the patient's respiratory and EKG cycles. The SYNC output signal of the trigger logic circuit 103 is coupled to a switch 444 which can be toggled between a SYNC position as shown and a "free-run" position in which the catheter position detection is not synchronized and the SYNC signal 107 is maintained at a logic high level, so that the X axis output signal 62 continuously tracks the input signal 328.

Figure 8:
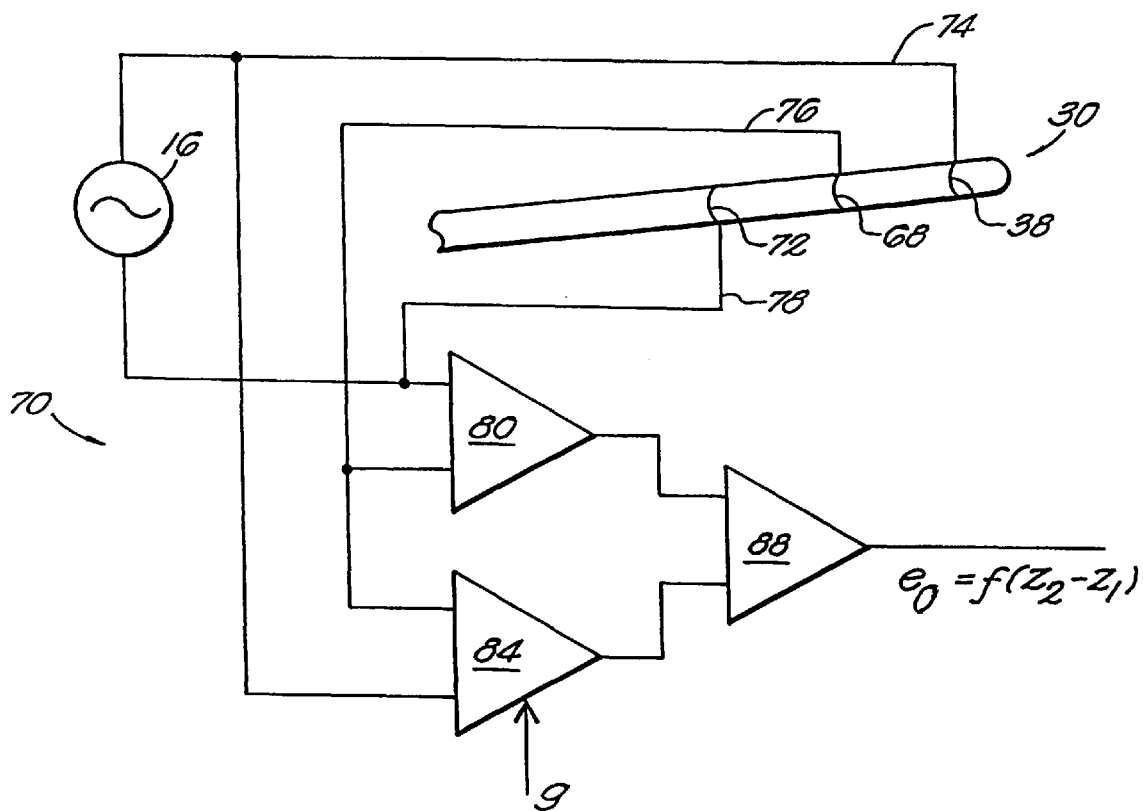
FIG. 8 is a schematic illustrating processing of signals from the detection, proximal and reference electrodes of the catheter of FIG. 1A in order to detect contact of the catheter with tissue.

Referring to FIG. 8, preferably, the signal processor 14 includes a catheter contact detection processor 70 for detecting contact of the catheter 30 with a vessel wall, or other tissue. Contact detection is achieved by providing a fourth current between the tip electrode 38 and the proximal electrode 72 and measuring the differential voltage representing impedance between the catheter electrodes, as described in U.S. Pat. No. 5,341,807 (Nardella) which is incorporated herein by reference.

More particularly, the energy source 16 is coupled between the tip electrode 38 and the proximal electrode 72 of the catheter to provide a current between the two electrodes. A first differential amplifier 80 has a first input coupled to the proximal electrode 72 and a second input coupled to the reference electrode 68. A second differential amplifier 84 has a first input coupled to the tip electrode 38 and a second input coupled to the reference electrode 68, as shown. With this arrangement, each of the differential amplifiers provides an output signal indicative of the impedance between the reference electrode 68 and a respective one of the proximal electrode 72 and tip electrode 38. The output of each of the differential amplifiers 80 and 84 is coupled to an input of a third differential amplifier 88 which detects a difference in the voltage representing a difference in the impedance between the tip electrode 38 and the reference electrode 68 and between the proximal electrode 72 and the reference electrode 68. When the impedance between electrodes 38 and 68 is substantially equal to the impedance between electrodes 68 and 72, the output of differential amplifier 88 is substantially null. Whereas, when the impedances differ (for example, as will occur when the tip electrode 38 contacts a vessel wall and the proximal electrode is disposed in blood), the output of the differential amplifier 88 increases. In this way, contact of the catheter 30 is indicated at the output of the differential amplifier 88 which may be coupled to a display (not shown).

Figure 9:
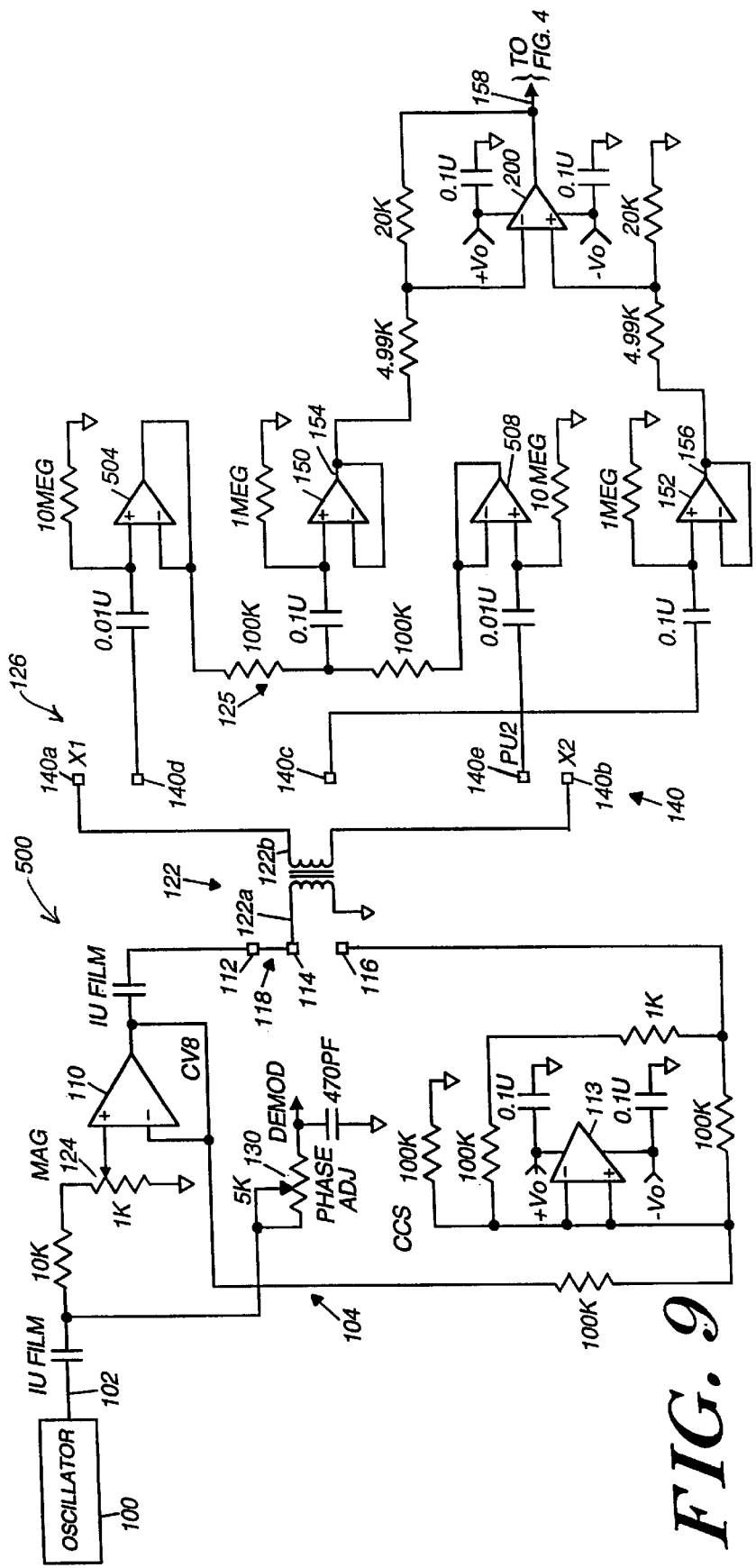
FIG. 9 is a schematic of an alternate front end circuit of the catheter positioning system of FIG. 2 including compensation electrodes for use in conjunction with externally attached reference electrodes.

Referring to FIG. 9, a schematic of an alternate front end circuit 500 of the catheter positioning system of FIG. 2 includes compensation electrodes for use in conjunction with externally attached reference electrodes 40a, 40b (FIG. 1). The front end circuit 500 is similar to the front end circuit 120 (FIG. 3), with like components being labeled with like reference numbers. Thus, the front end circuit 500 includes the gain and/or phase stage 104, the electrode interface 126, buffers 150 and 152, and differential amplifier 200.

The front end circuit 500 differs from the front end circuit 120 of FIG. 3 in that the circuit 500 includes two additional electrodes, referred to as compensation electrodes PU1 and PU2, which are pad electrodes attached externally to the patient and electrically coupled to the signal processor via terminals 140d, 140e of connector 140. The compensation electrodes PU1 and PU2 are coupled to amplifiers 504 and 508, respectively, each of which has a high input impedance. Amplifier 504 has a non-inverting input capacitively coupled to the input terminal 140d and an inverting input coupled to its output. The output of amplifier 504 is further coupled to the resistor divider 125 (FIG. 3). Similarly, amplifier 508 has a non-inverting input capacitively coupled to the input terminal 140e and an inverting input coupled to its output. The output of amplifier 508 is further coupled to the resistor divider 125. Use of the compensation electrodes PU1 and PU2 serves to minimize any impedance variations associated with external attachment of the reference electrodes 40a, 40b to the patient.

Figure 10:
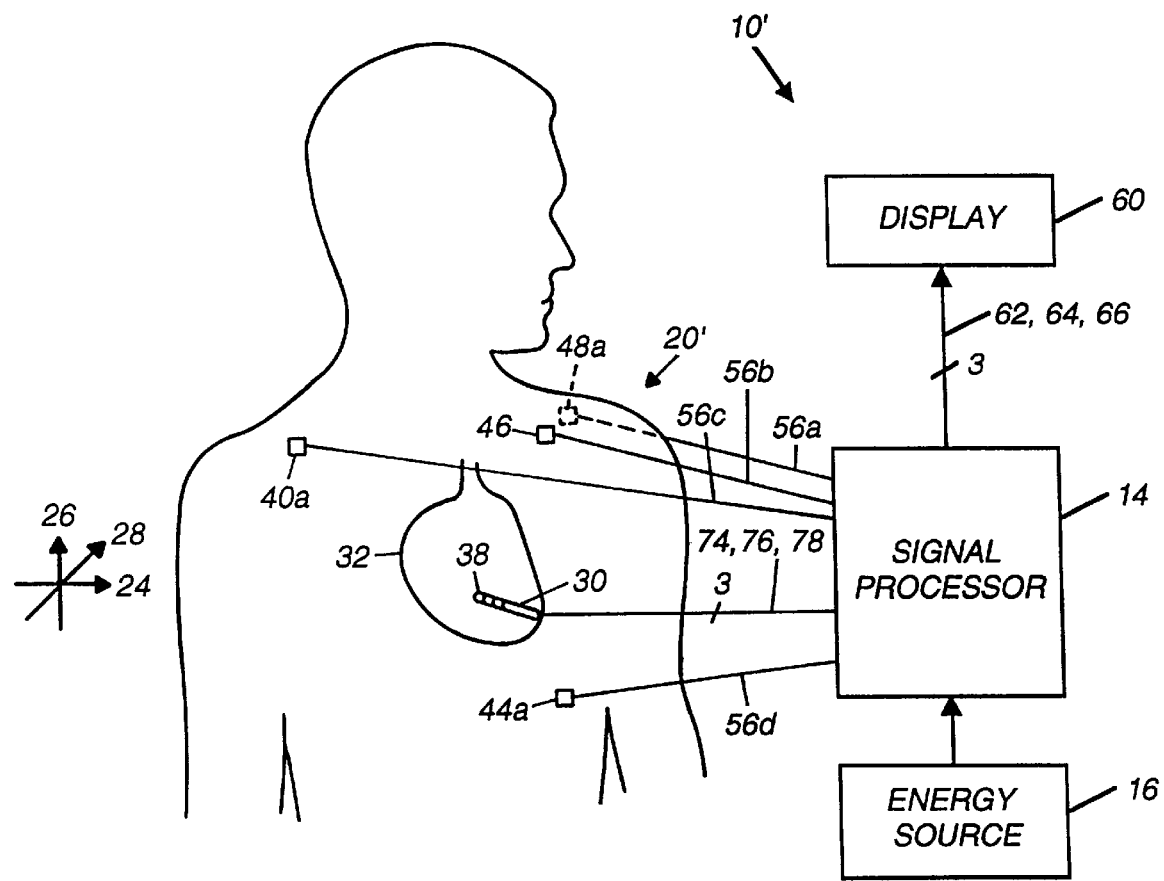
FIG. 10 illustrates an alternate catheter positioning system utilizing four surface excitation electrodes.

Referring to FIG. 10, in which like reference numbers refer to like elements, an alternate catheter mapping system 10' utilizes only four excitation, or reference electrodes 40a, 44a, 48a, and 46 (collectively 20') positioned on the surface of the patient for detecting the position of the detection electrode 38 supported by the catheter 30. This is achieved by using one of the four electrodes 20' as common to each of the three axes of excitation. Specifically, one of the electrodes 40a is an X axis electrode and the return path for the current applied along the X axis is provided by a common electrode 46. Another electrode 44a is a Y axis electrode and the return path for the current applied along the Y axis is provided by the common electrode 46 and the last electrode 48a is a Z axis electrode and the return path for the current applied along the Z axis is provided by the common electrode. Thus, a first current having a first frequency passes between X axis electrodes 40a and 46, a second current having a second frequency passes between Y axis electrodes 44a and 46 and a third current having a third frequency passes between Z axis electrodes 48a and 46.

The same signal processing circuitry 14 (FIG. 2) used to process the signals 42a–42f from the six excitation electrodes 20 in FIG. 1 can be used to process the signals 56a–56d from the four excitation electrodes 40a, 44a, 48a, and 46. More particularly, the excitation electrodes 20' are coupled to the signal processor 14 by coupling the X axis excitation electrode 40a to one input of the X axis processor unit 50 (e.g., connector terminal 140a in FIG. 2) and the common electrode 46 to the other input of the X axis processor unit 50 (e.g., connector terminal 140b in FIG. 2). Similarly, the Y axis excitation electrode 44a is coupled to one input of the Y axis processor unit 52 and the common electrode 46 is coupled to the other input of the Y axis processor unit 52. Further, the Z axis excitation electrode 48a is coupled to one input of the Z axis processor unit 54 and the common electrode 46 is coupled to the other input of the Z axis processor unit 54. With this arrangement, two additional electrodes and their associated inaccuracies (e.g., due to inadvertent electrode movement and/or the impedance associated with surface electrodes) are eliminated.

Figure 11:
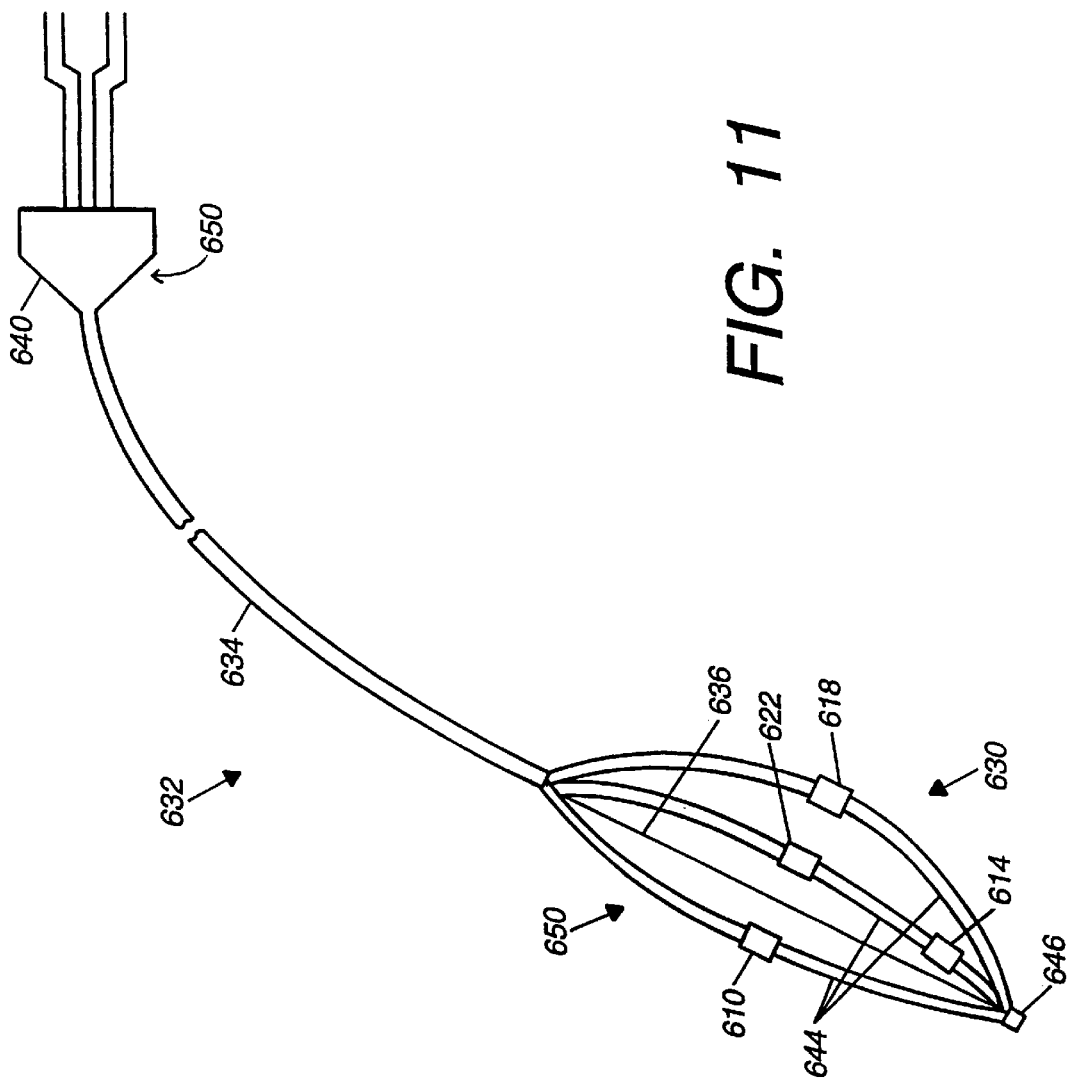
FIG. 11 illustrates an intracardiac catheter supporting four excitation electrodes in accordance with a further embodiment of the invention.

Referring to FIG. 11, an intracardiac catheter 632 supporting a plurality of electrodes 610, 614, 618, 622 (collectively 630) for use as excitation electrodes is shown. The catheter 632 is adapted for insertion through a vessel into a patient's heart. The catheter 632 has a plurality of flexible electrode supporting members 644, which may be provided in the form of wires, disposed at the end of a flexible tube 634. The electrode supporting members 644 are coupled together at a distal end 646 of the catheter which is attached to a pull wire 636. The pull wire 636 extends through the flexible tube 634 to the proximal end 650 of the catheter. Wire conductors coupled to the electrodes 630 extend through the tube 634 to terminate at a connector 640 through which the electrodes are connected to an energy source which generates the excitation signals.

As the catheter 632 is inserted into a chamber of the patient's heart through a vessel, the flexible electrode supporting members 644 are pulled together (not shown). Once the catheter 632 is positioned at a desired location, the wire 636 is pulled from the proximal end 650 of the catheter (not shown), outside of the patient. Actuation of the wire 636 causes the flexible electrode supporting members 644 to bow outward, as shown, to form a basket, or cage structure 650. In use, some or all of the electrodes 630 may contact the chamber wall, although such contact is not necessary for catheter position detection. It may however be desirable to have the at least a portion of the basket structure 650 contact a chamber wall in order to stabilize the catheter and synchronize the excitation electrodes relative to cardiac movements.

The four excitation electrodes 630 are paired in the same way as the four surface excitation electrodes of FIG. 10 to provide three intersecting excitation axes. Specifically, electrode 610 provides a first X axis electrode and the common electrode 622 provides the second X axis electrode, electrode 618 provides a first Y axis electrode and the common electrode 622 provides the second Y axis electrode, and electrode 614 provides a first Z axis electrode and the common electrode 622 provides the second Z axis electrode. Thus, the wire conductors extending from each of the electrodes to the connector 640 can be coupled to a signal processor of the type shown in FIG. 2 in the manner discussed above in conjunction with FIG. 10.

In use, the detection electrode 38 (FIG. 1) is positioned in a location of the heart to be detected. Significantly, the detection electrode 38 need not be positioned within the region defined by the basket 650, although it can be. More particularly, because the electric field generated by passing an AC signal between a pair of excitation electrodes extends well beyond the straight line path between the electrodes in a conductive medium, the detection electrode 38 may in fact be located external to the basket 650. The detection electrode 38 need only be at a location in which it is subjected to the three electric fields generated by the three sets of excitation electrodes. In fact, the basket 650 may be located in one chamber of the heart, for example, the easier accessible right ventricle, and the detection electrode 38 located in the left ventricle where position detection for treatment, such as ablation, is desired.

Figure 12:
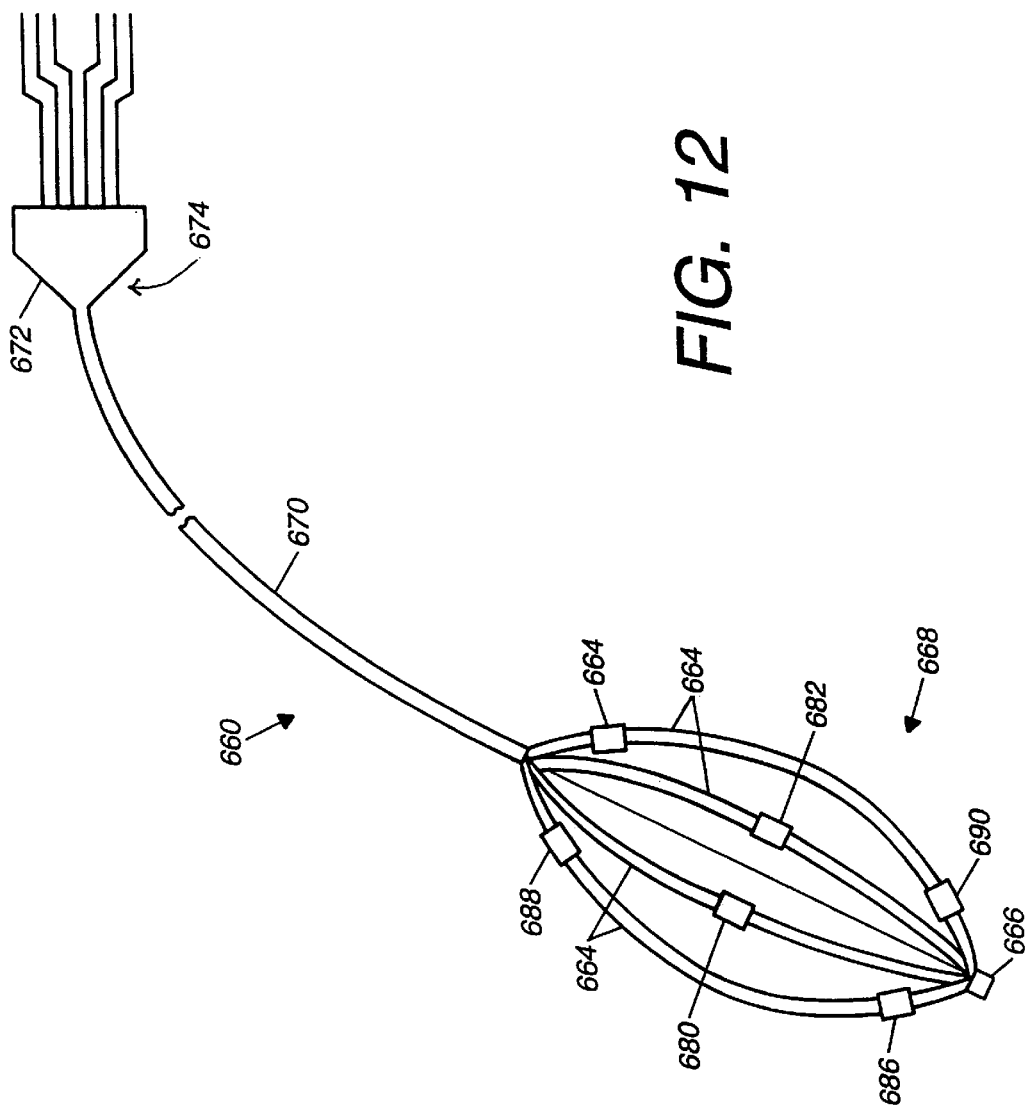
FIG. 12 illustrates an alternate intracardiac catheter supporting six intracardiac excitation electrodes in accordance with a still further embodiment of the invention.

Referring to FIG. 12, an alternate intracardiac catheter 660 includes a plurality of electrode supporting members 664 coupled together at a distal end 666 of the catheter for supporting a plurality of excitation electrodes 668. The catheter 660 further includes a flexible tube 670 through which wire conductors coupled to the electrodes 668 extend. The wire conductors terminate at a connector 672 at the proximal end 674 of the catheter for permitting electrical connections to be made to the electrodes 668.

The catheter 660 differs from the catheter 632 of FIG. 11 in that the former supports six excitation electrodes 668 and the latter supports four excitation electrodes as described above. More particularly, the catheter 660 has a pair of X axis excitation electrodes 680, 682, a pair of Y axis excitation electrodes 684, 686, and a pair of Z axis excitation electrodes 688, 690. The excitation electrodes 668 supported by the catheter 660 may be coupled to a signal processor of the type and in the manner described above in conjunction with FIG. 2.

As will be appreciated by those of ordinary skill in the art, current density is greatest at the excitation electrodes and decreases as you move away from the electrodes, to a point of lowest current density half-way between two excitation electrodes in a given axis. This phenomena results in the greatest voltage gradient, and output sensitivity occurring when the detection electrode 38 is in close proximity to one of the excitation electrodes and also results in a non-linearity in the gain of the system relative to the excitation electrodes. Further, such non-linearity is exacerbated when the excitation electrodes are located close to one another, as occurs with intracardiac excitation electrodes as compared to surface excitation electrodes.

In catheter repositioning applications, this non-linearity is generally not of concern. This is because catheter repositioning is not dependent on the consistency of system gain, but rather on determining the difference between two or more detected positions in order to enable the operator to reposition the catheter at a point of interest.

However, in other applications, it may be desirable to determine the absolute distance between detected catheter positions. This can be achieved with the use of an additional electrode on the catheter 30 (FIG. 1) located at a fixed, known distance from the detection electrode 38 or with a separate "calibration" electrode provided for reconciling the distance/voltage associated with movement of the catheter 30. Such absolute distance calibration requires three measurements to be made, with the detection electrode 38 located at three different positions relative to the excitation electrodes.

More particularly, assuming that the body between the excitation electrodes behaves linearly, the location of a detection electrode along any measured axis will be a constant multiplied by the voltage differential measured in the direction of that axis. With two electrodes placed a known distance apart on the catheter 30, the voltages measured in each axis for the two electrodes can be related to the known distance between the electrodes. The measurement of three data points then permits the three constants associated with voltage measurements in each of the three excitation axes to be determined and used to calibrate catheter position detection. Thus, with this arrangement, the absolute distance between two or more detected catheter positions can be determined.

In applications in which improved linearity or determination of the absolute distance between catheter positions is desired, various techniques can be used to compensate for non-linearity in the detected signals resulting from non-linearities in the electric fields. As one example, the technique noted above, of locating the excitation catheter in one heart ventricle and detecting position with an intracardiac electrode in another heart ventricle may reduce non-linearity since, the further away the detection electrode is moved from the excitation electrodes, the lower the voltage gradient and the more linear the electric fields.

As another alternative, the system gain may be set to a relatively high level which ensures that the detection sensitivity is at a minimum desired level, such as on the order of one millimeter, when the detection electrode 38 is positioned at a point of least sensitivity (i.e., midway between a pair of excitation electrodes for a given axis). A suitable system gain can be determined empirically based on the size and shape of the excitation electrodes and characteristics of the patient's heart chambers. With this arrangement, while catheter position can be determined to within a predetermined minimum value, such as one millimeter, when the detection electrode is located at the least sensitive location, midway between a pair of excitation electrodes for a given axis, catheter position is determined with even greater accuracy at locations closer to one of the excitation electrodes.

As a still further alternative technique for compensating for the non-linearity in the gain of the detected signals resulting from electric field non-linearities, the gain of the detection circuitry may be boosted as the catheter approaches positions of least sensitivity (i.e., at or near the midpoint between a pair of excitation electrodes, when the signal processor output approaches null). For example, the output of the signal processor 14 may be monitored for the signal gain to fall below a predetermined threshold or to a minimum and/or for the signal to approach null. Once one or both of these conditions occurs, the system gain may be boosted. More particularly, the system gain may be boosted by a predetermined amount or, alternatively, may be boosted incrementally or continuously, as the output signal gain falls below the predetermined level and/or approaches null.

System gain in such a system may be boosted in various ways. For example, the gain of one or more amplifiers within the signal processor 14, such as the differential amplifier 200 (FIG. 4), may be boosted. Alternatively, the current level of the excitation signals may be boosted.

Figure 13:
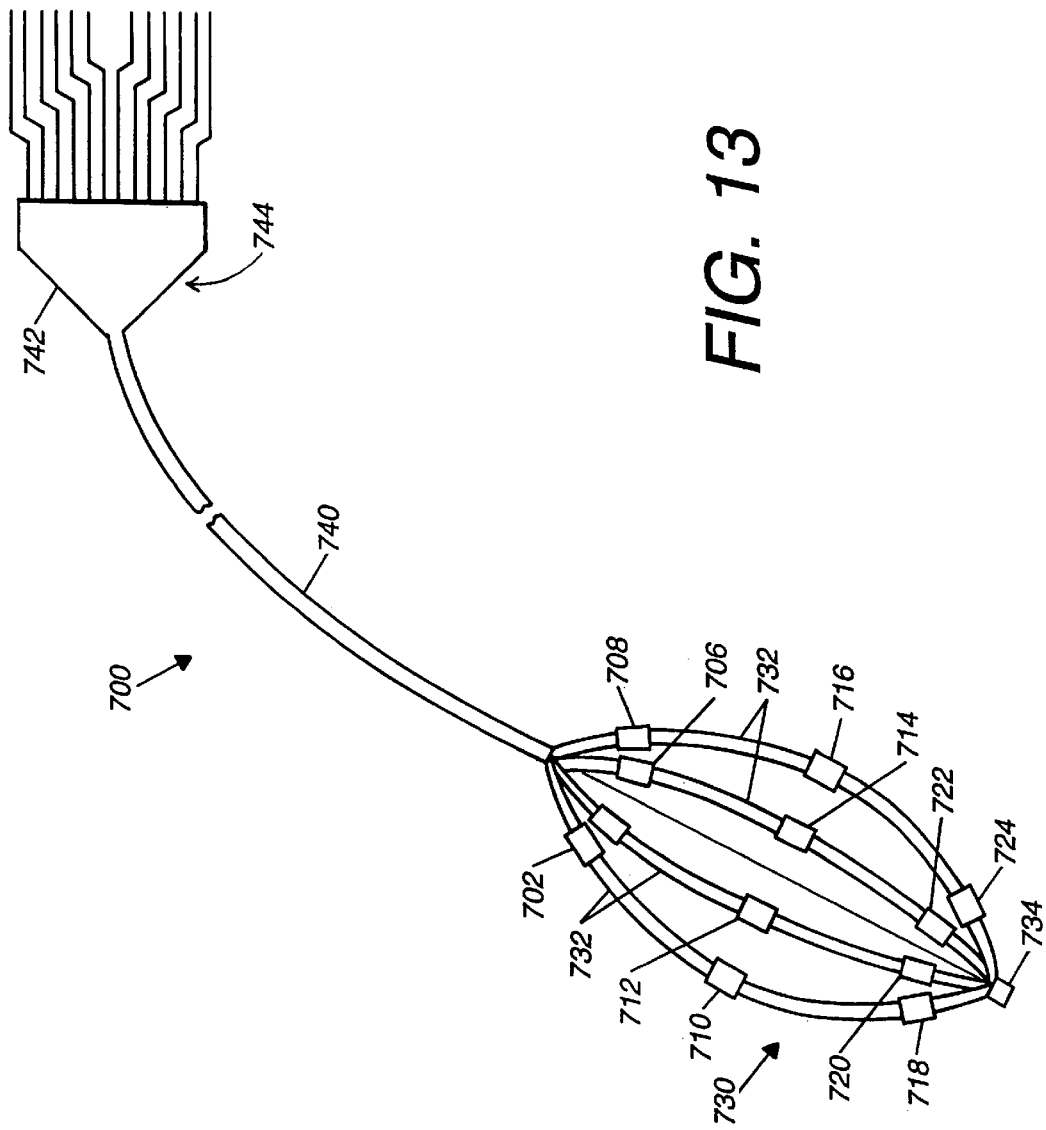
FIG. 13 illustrates an further alternate intracardiac catheter supporting twelve intracardiac excitation electrodes in accordance with another embodiment of the invention.

A further technique for compensating for electric field non-linearities includes the use of an intracardiac catheter 700 supporting twelve electrodes 702–724 (collectively 730), as shown in FIG. 13. The intracardiac catheter 700 includes a plurality of electrode supporting members 732 coupled together at a distal end 734 of the catheter for supporting the excitation electrodes 730. The catheter 700 further includes a flexible tube 740 covering wire conductors coupled to and extending from the electrodes. The wire conductors terminate at a connector 742 at the proximal end 744 of the catheter for permitting electrical connections to be made to the electrodes 730.

The twelve excitation electrodes 730 establish two X, Y, Z coordinate systems. A first X, Y, Z coordinate system is defined by a pair of X axis electrodes 708, 718, a pair of Y axis electrodes 702, 724, and a pair of Z axis electrodes 712, 714. A second X, Y, Z coordinate system is defined by a pair of X axis electrodes 706, 720, a pair of Y axis electrodes 704, 722 and a pair of Z axis electrodes 710, 716. Each of the pairs of excitation electrodes is coupled to a respective signal processor unit (like signal processor units 50, 52, 54 of FIG. 2), as shown in FIG. 14.

In use, at any given time, catheter position detection is achieved by applying an excitation signal along each of the three intersecting axes defined by excitation electrodes of a selected one of the coordinate systems and sensing the differential voltage indicative between the detection electrode 38 and each pair of excitation electrodes of the selected, active coordinate system, as described further below. However, when the detection electrode 38 approaches one of the excitation electrodes of the selected coordinate system, the excitation coordinate system may be switched to the other coordinate system. Such switching may be achieved with a multiplexer arrangement as shown in FIG. 14.

Figure 14:
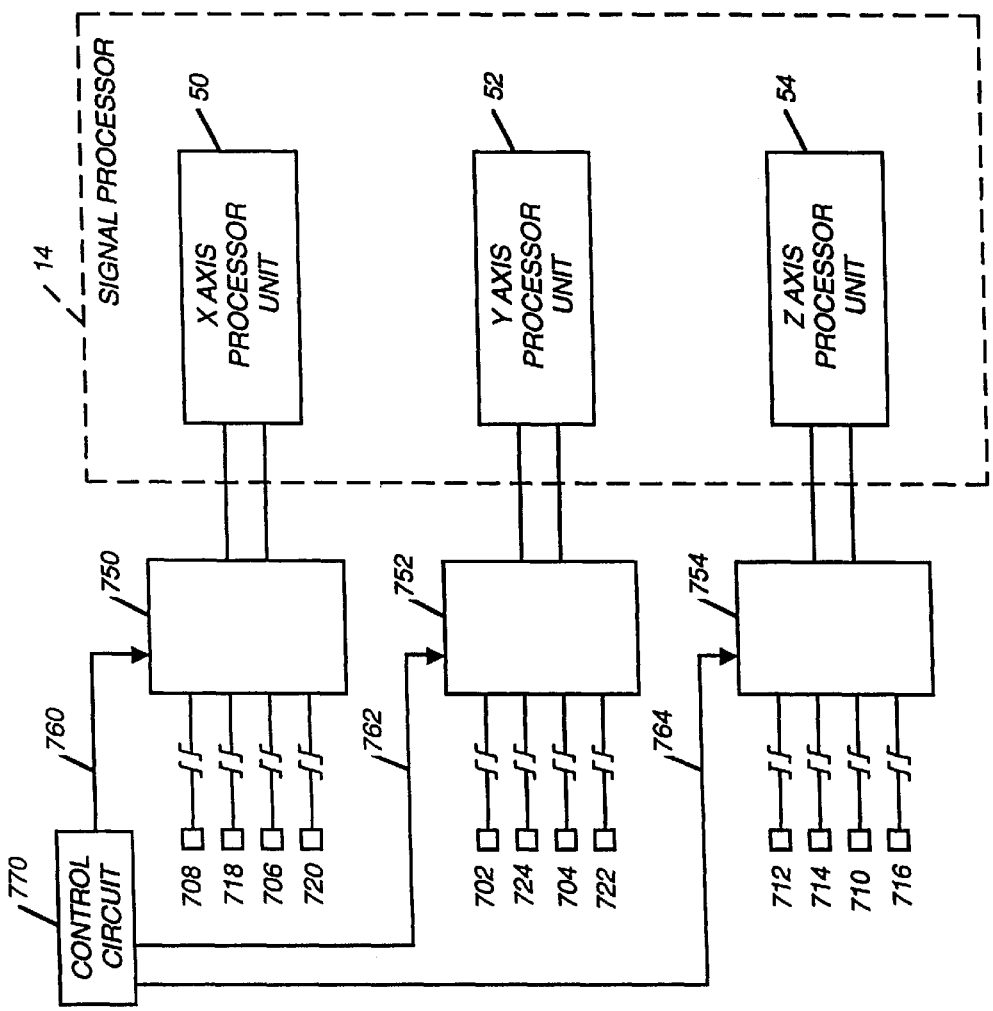
FIG. 14 is a schematic of a signal processor and multiplexer circuit suitable for use with the intracardiac catheter of FIG. 13.

Referring to FIG. 14, multiplexers 750, 752 and 754 couple the excitation electrodes of the selected one of the X, Y, Z coordinate systems to the X axis processor unit 50 (FIG. 2), the Y axis processor unit 52 (FIG. 2), and the Z axis processor unit 54 (FIG. 2) of the signal processor 14. The multiplexers 750, 752, 754 are synchronized so that when multiplexer 750 couples the X axis electrodes 708, 718 of the first coordinate system to the X axis processor unit 50, multiplexer 752 couples Y axis electrodes 702, 724 of the first coordinate system to the Y axis processor unit 52 and multiplexer 754 couples Z axis electrodes 712, 714 of the first coordinate system to the Z axis processor unit 54. Conversely, when multiplexer 750 couples the X axis electrodes 706, 720 of the second coordinate system to the X axis processor unit 50, multiplexer 752 couples Y axis electrodes 704, 722 of the second coordinate system to the Y axis processor unit 52 and multiplexer 754 couples Z axis electrodes 710, 716 of the second coordinate system to the Z axis processor unit 54.

The multiplexers 750, 752, 754 are responsive to a control circuit 770, such as may be provided by a microprocessor, for coupling excitation electrodes from a selected one of the coordinate systems to the signal processor 14. More particularly, the control circuit 770 provides control signals 760, 762, 764 to the multiplexers 750, 752, 754, respectively, to cause the multiplexers to switch between one excitation coordinate system and the other when the detection electrode approaches one of the excitation electrodes of the active coordinate system (i.e., when the system output signal is furthest from null).

In one embodiment, control circuit 770 signals multiplexers 750, 752, 754 to switch to an alternate coordinate system when the detection electrode is within one quarter of the axial distance from one of a pair of active excitation electrodes defining a given axis. This may be accomplished by providing a threshold reference signal corresponding to one quarter of the distance along a given axis from each excitation electrode defining that axis. When the voltage difference measured at the detection electrode crosses the threshold reference value in a direction toward an excitation electrode, the alternate coordinate system is used. Threshold reference signals may be provided by applying resistor dividers such as, and in the same location as, resistor divider 125 (FIG. 3). By applying resistor dividers having one quarter values (such as one divider having 50K and 150K ohm resistors and a second divider having 150K and 50K resistors) between the same signals as resistor divider 125, threshold reference signals having the desired values may be provided and coupled to control circuit 770. While the values provided in this exemplary embodiment will serve to keep the catheter positioning systems described herein in a generally linear operating region, a person of ordinary skill in the art will recognize that other threshold signals may be used consistent with the invention.

It will be appreciated by those of ordinary skill in the art that the benefits achieved with the twelve excitation electrode embodiment of FIG. 13 may likewise be achieved with as few as eight electrodes, when using the "common" electrode technique discussed in conjunction with FIGS. 10 and 11. It will be further appreciated that more than the two coordinate systems provided by twelve electrodes may be used. For example, an additional six electrodes would provide a third X, Y, Z coordinate system for use in the manner described above.

The above-described techniques which compensate for electric field non-linearities and which render the intracardiac excitation electrode embodiments well suited for absolute catheter distance determination, are useful in transmyocardial revascularization/percutaneous myocardial revascularization (TMR/PMR) applications. In TMR/PMR applications, it is beneficial to precisely detect the distance between a border of a lesion and a location to form a channel to permit blood flow to a recoverable region surrounding the lesion. The lesion border is generally located using fluoroscopic techniques. With the improved linearity resulting from the techniques described herein, the catheter positioning system may be able to mimic the shape of the lesion border provided by fluoroscopic techniques. Multiple points on the border may then be recorded and channel formation locations spaced by a predetermined distance from the lesion border can be located using the catheter positioning techniques described herein.

Embodiments utilizing eight or more excitation electrodes (i.e., two or more X, Y, Z coordinate systems) provide an additional advantage of permitting a cardiac chamber to be outlined quickly. Such an outline may be obtained by designating the electrodes of one of the coordinate systems to be the excitation electrodes and the electrodes of the other coordinate system to be the detection, or mapping electrodes. The designations of the electrodes as "excitation" or "detection" can then be swapped, resulting in twelve data points which may be used to generate a graphical image of the cardiac chamber.

The use of intracardiac excitation electrodes provides several advantages as compared to surface excitation electrodes. First, a higher signal to noise ratio is generally achieved since greater signal magnitudes (assuming the same signal source) flow through the region of interest due to the position of the excitation electrodes within the region of interest. Further, inaccuracies due to the impedance between the surface electrodes and the skin, as well as inaccuracies due to inadvertent movement of the surface electrodes, are eliminated. Additionally, the catheter supporting the excitation electrodes may serve additional purposes. For example, the excitation electrodes themselves may perform cardiac sensing functions, such as ECG sensing. Further, the excitation electrodes and/or other electrodes (not shown) supported by the same catheter may perform cardiac pacing and/or ablation functions.

It will be appreciated by those of ordinary skill in the art that the apparatus and techniques described herein may be used to detect the position of multiple detection electrodes which may be supported by a single catheter or, alternatively, may be supported by separate catheters. The signal processor of a multiple detection electrode system may comprise additional processor units (like processor units 50, 52, and 54 shown in FIG. 2) for each additional detection electrode. Alternatively, the signal processor units 50, 52 and 54 may be multiplexed to detect the position of the multiple detection electrodes. In addition to detection of the position of the multiple detection electrodes, this arrangement advantageously permits the direction of the electrodes to be determined. One application for such a system is atrial fibrillation, in which an elongated continuous lesion is created.

In general, the catheter positioning techniques of the present invention require, at a minimum, three excitation signals to be applied in three intersecting (i.e., non-parallel) planes. While some of the above-disclosed embodiments utilize excitation signals in mutually orthogonal planes (i.e., along three mutually orthogonal axes), the excitation signals may be applied in three orthogonal or non-orthogonal planes, such as planes separated by between 30–90 degrees. In catheter repositioning applications, perhaps the most robust applications of the system of the invention, axis orthogonality is of less concern than in absolute positioning applications. The ability to use non-orthogonal excitation signals reduces the need to precisely place surface excitation electrodes or to rely on precise geometries of an intracardiac excitation catheter.

The use of non-orthogonal excitation signals reduces signal gain somewhat. In some applications, it may be desirable to compensate for such gain reduction. One way to compensate for the gain reduction associated with non-orthogonal excitation signals is to mathematically correct for the non-orthogonality of the AC signals. However, this technique is possible only if the angles between the three excitation axes are known. In applications using eight or more intracardiac excitation electrodes which define at least two X, Y, Z coordinate systems, gain reduction can be compensated, at least in part, by selecting the excitation coordinate system which comes closest to providing orthogonal excitation signals. In practice, exact determinations of the angles between the three excitation axes are difficult, but measurement of angles may be aided by the application of fluoroscopic techniques or by using alternate X, Y, Z coordinate systems to locate the excitation electrodes of the other coordinate system.

It will be appreciated by those of ordinary skill in the art that the techniques described herein may be practiced with the use of various excitation electrode types and configurations. For example, it will be apparent to those of ordinary skill in the art, that multiple intracardiac catheters, each supporting less than all of excitation electrodes for the particular application, or a combination of intracardiac and surface excitation electrodes, may be used to establish three excitation signals in three intersecting planes.

The foregoing description of the illustrative embodiments of the invention is presented to indicate the range of constructions to which the invention applies. Variations in the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. An apparatus for detecting a position of a catheter in contact with a patient, wherein the catheter includes a detection electrode and said position is characterized by an X coordinate relative to an X axis, a Y coordinate relative to a Y axis, and a Z coordinate relative to a Z axis, said apparatus comprising:
    an X axis excitation electrode;
    a Y axis excitation electrode;
    a Z axis excitation electrode;
    a common excitation electrode;
    a signal generator adapted for applying a first excitation signal between the X axis excitation electrode and the common electrode, a second excitation signal between the Y axis excitation electrode and the common electrode, and a third excitation signal between the Z axis excitation electrode and the common electrode; and
    a signal processor for measuring the differential voltage indicative of impedance between the detection electrode and X axis excitation electrode and the common electrode in order to determine the X coordinate, the differential voltage indicative of impedance between the detection electrode and the Y axis excitation electrode and the common electrode in order to determine the Y coordinate, and the differential voltage indicative of impedance between the detection electrode and the Z axis excitation electrode and the common electrode in order to determine the Z coordinate.

2. The apparatus of claim 1 wherein the X axis excitation electrode, the Y axis excitation electrode, the Z axis excitation electrode, and the common electrode are surface electrodes adapted for external attachment to the patient.

3. The apparatus of claim 1 wherein the X axis excitation electrode, the Y axis excitation electrode, the Z axis excitation electrode, and the common electrode are subcutaneous electrodes adapted for insertion into the patient.

4. The apparatus of claim 1 wherein the X axis excitation electrode, the Y axis excitation electrode, the Z axis excitation electrode, and the common electrode are intracardiac electrodes adapted for insertion into the cardiac regions of the patient.

5. The apparatus of claim 1 wherein the first excitation signal has a first frequency, the second excitation signal has a second frequency, and the third excitation signal has a third frequency.

6. A method for detecting a position of a catheter in contact with a patient, said catheter including a detection electrode and said position being characterized by an X coordinate relative to an X axis, a Y coordinate relative to a Y axis, and a Z coordinate relative to a Z axis, said method comprising the steps of:
    applying a first excitation signal to the patient generating a first electric field between an X axis excitation electrode and a common electrode disposed along the X axis;
    applying a second excitation signal to the patient generating a second electric field between a Y axis excitation electrode and the common electrode disposed along the Y axis;
    applying a third excitation signal to the patient generating a third electric field between a Z axis excitation electrode and the common electrode disposed along the Z axis;
    locating the catheter so that the detection electrode is disposed in the patient within the first, second, and third electric fields; and
    measuring the differential voltage between the detection electrode and the X axis excitation electrode and the common electrode to determine the X coordinate, measuring the differential voltage between the detection electrode and the Y axis excitation electrode and the common electrode to determine the Y coordinate, and measuring the differential voltage between the detection electrode and the Z axis excitation electrode and the common electrode to determine the Z coordinate thereby determining the X, Y and Z coordinates of the catheter.

7. The method of claim 6 further comprising the step of providing the X axis excitation electrode, the Y axis excitation electrode, the Z axis excitation electrode, and the common electrode as surface electrodes adapted for external attachment to the patient.

8. The method of claim 6 further comprising the step of providing the X axis excitation electrode, the Y axis excitation electrode, the Z axis excitation electrode, and the common electrode as subcutaneous electrodes adapted for insertion into the patient.

9. The method of claim 6 further comprising the step of providing the X axis excitation electrode, the Y axis excitation electrode, the Z axis excitation electrode, and the common electrode as intracardiac electrodes adapted for insertion into the cardiac regions of the patient.

10. The method of claim 6 wherein the first excitation signal applying step comprises providing the first excitation signal with a first frequency, the second excitation signal providing step comprises providing the second excitation signal with a second frequency, and the third excitation signal providing step comprises providing the third excitation signal with a third frequency.

11. An apparatus for detecting a position of a catheter in contact with a patient, said catheter including a detection electrode and said position being characterized by an X coordinate relative to an X axis, a Y coordinate relative to a Y axis, and a Z coordinate relative to a Z axis, said apparatus comprising:

a pair of X axis intracardiac excitation electrodes disposed along the X axis;

a pair of Y axis intracardiac excitation electrodes disposed along the Y axis;

a pair of Z axis intracardiac excitation electrodes disposed along the Z axis; and a signal processor for measuring the differential voltage indicative of impedance between the detection electrode and each electrode of the pair of X axis intracardiac excitation electrodes in order to determine the X coordinate, the differential voltage indicative of impedance between the detection electrode and each electrode of the pair of Y axis intracardiac excitation electrodes in order to determine the Y coordinate, and the differential voltage indicative of impedance between the detection electrode and each electrode of the pair of Z axis intracardiac excitation electrodes in order to determine the Z coordinate.

12. The apparatus of claim 11 wherein each of the first, second and third pairs of intracardiac excitation electrodes shares a common electrode.

13. The apparatus of claim 11 further comprising:

a second pair of X axis intracardiac excitation electrodes disposed along a second X axis;

a second pair of Y axis intracardiac excitation electrodes disposed along a second Y axis; and a second pair of Z axis intracardiac excitation electrodes disposed along a second Z axis.

14. The apparatus of claim 13 wherein the signal processor is adapted for being selectively coupled to either the first pair of X axis electrodes, the first pair of Y axis electrodes, and the first pair of Z axis electrodes or to the second pair of X axis electrodes, the second pair of Y axis electrodes, and the second pair of Z axis electrodes.

15. A method for detecting a position of a catheter in contact with a patient, said position characterized by an X coordinate relative to an X axis, a Y coordinate relative to a Y axis and a Z coordinate relative to a Z axis, comprising the steps of:

positioning a detection electrode on the catheter;

positioning a pair of X axis intracardiac excitation electrodes along the X axis;

applying a first excitation signal between the X axis intracardiac excitation electrodes;

positioning a pair of Y axis intracardiac excitation electrodes along the Y axis;

applying a second excitation signal between the Y axis intracardiac excitation electrodes;

positioning a pair of Z axis intracardiac excitation electrodes along the Z axis;

applying a third excitation signal between the Z axis intracardiac excitation electrodes;

measuring the differential voltage indicative of impedance between the detection electrode and each electrode of the X axis intracardiac excitation electrodes in order to determine the X coordinate;

measuring the differential voltage indicative of impedance between the detection electrode and each electrode of the Y axis intracardiac excitation electrodes in order to determine the Y coordinate; and measuring the differential voltage indicative of impedance between the detection electrode and each electrode of the Z axis intracardiac excitation electrodes in order to determine the Z coordinate.

16. The method of claim 15 further comprising the step of providing one of each of the X axis intracardiac excitation electrodes, the Y axis intracardiac excitation electrodes, and the Z axis intracardiac excitation electrodes as a common electrode.

17. The method of claim 15 further comprising the steps of:

positioning a second pair of X axis intracardiac excitation electrodes along a second X axis;

positioning a second pair of Y axis intracardiac excitation electrodes along a second Y axis; and positioning a second pair of Z axis intracardiac excitation electrodes along a second Z axis.

18. The method of claim 17 further comprising the steps of:

measuring the differential voltage indicative of impedance between the detection electrode and each electrode of the second pair of X axis intracardiac excitation electrodes in order to determine the X coordinate;

measuring the differential voltage indicative of impedance between the detection electrode and each electrode of the second pair of Y axis intracardiac excitation electrodes in order to determine the Y coordinate;

measuring the differential voltage indicative of impedance between the detection electrode and each electrode of the second pair of Z axis intracardiac excitation electrodes in order to determine the Z coordinate; and selecting either the X, Y and Z coordinates determined from differential voltage measurements using the pairs or X-, Y- and Z- axis intracardiac excitation electrodes, or the X, Y and Z coordinates determined from differential voltage measurements using the second pairs of X-, Y- and Z- axis intracardiac excitation electrodes.

19. A method for detecting a position of a catheter in contact with a patient, said position characterized by an X coordinate relative to an X axis, a Y coordinate relative to a Y axis and a Z coordinate relative to a Z axis, comprising the steps of:

positioning a detection electrode on the catheter;

positioning a pair of X axis excitation electrodes along the X axis;

applying a first excitation signal between the X axis excitation electrodes;

positioning a pair of Y axis excitation electrodes along the Y axis;

applying a second excitation signal between the Y axis excitation electrodes;

positioning a pair of Z axis excitation electrodes along the Z axis;

applying a third excitation signal between the Z axis excitation electrodes;

determining the X coordinate by measuring the voltage between the detection electrode and a reference potential derived from the pair of X axis excitation electrodes;

determining the Y coordinate by measuring the voltage between the detection electrode and a reference potential derived from the pair of Y axis excitation electrodes; and determining the Z coordinate by measuring the voltage between the detection electrode and a reference potential derived from the pair of Z axis excitation electrodes.

20. A method for detecting a position of a catheter in contact with a patient, said position characterized by an X coordinate relative to an X axis, a Y coordinate relative to a Y axis and a Z coordinate relative to a Z axis, comprising the steps of:

- positioning a detection electrode on the catheter;
- positioning a pair of X axis excitation electrodes along the X axis;
- applying a first excitation signal between the X axis excitation electrodes;
- positioning a pair of Y axis excitation electrodes along the Y axis;
- applying a second excitation signal between the Y axis excitation electrodes;
- positioning a pair of Z axis excitation electrodes along the Z axis;
- applying a third excitation signal between the Z axis excitation electrodes;
- determining the X coordinate by measuring a first voltage between the detection electrode and a first electrode of the pair of X axis excitation electrodes, measuring a second voltage between the detection electrode and a second electrode of the pair of X axis excitation electrodes and determining the difference between the first and second measured voltages;
- determining the Y coordinate by measuring a third voltage between the detection electrode and a first electrode of the pair of Y axis excitation electrodes, measuring a fourth voltage between the detection electrode and a second electrode of the pair of Y axis excitation electrodes and determining the difference between the third and fourth measured voltages; and
- determining the Z coordinate by measuring a fifth voltage between the detection electrode and a first electrode of the pair of Z axis excitation electrodes, measuring a sixth voltage between the detection electrode and a second electrode of the pair of Z axis excitation electrodes and determining the difference between the fifth and sixth measured voltages.

21. A method for detecting position of a treatment catheter in a patient's heart, said treatment catheter including a detection electrode and said position being characterized by an X coordinate relative to an X axis, a Y coordinate relative to a Y axis and a Z coordinate relative to a Z axis, wherein the method comprises the steps of:

- positioning a basket catheter in a chamber of the patient's heart, said basket catheter having a plurality of flexible electrode-carrying arm members that bow outwardly to position electrodes in contact with a wall of the chamber and stabilize the basket catheter in the chamber, wherein electrodes of said arm members are operative for sensing cardiac signals,
- selectively exciting plural ones of said electrodes as X axis excitation electrodes, Y axis excitation electrodes and Z axis excitation electrodes, respectively, to define electric fields in the heart, and
- determining the X coordinate, the Y coordinate and the Z coordinate of the treatment catheter by measuring voltages between the detection electrode of the treatment catheter and the selectively excited ones of said electrodes of the basket catheter.

* * * * *